(12) United States Patent
Hamada

(10) Patent No.: US 6,436,101 B1
(45) Date of Patent: Aug. 20, 2002

(54) RASP FOR USE IN SPINE SURGERY

(76) Inventor: James S. Hamada, 325 9th St., Manhattan Beach, CA (US) 90266

( * ) Notice: Subject to any disclaimer, the term of this patent is extended or adjusted under 35 U.S.C. 154(b) by 0 days.

(21) Appl. No.: 09/545,401

(22) Filed: Apr. 7, 2000

Related U.S. Application Data

(63) Continuation-in-part of application No. 09/416,922, filed on Oct. 13, 1999.

(51) Int. Cl.⁷ .............................................. A61B 17/22
(52) U.S. Cl. ........................................................ 606/85
(58) Field of Search .............................. 606/85, 84, 53, 606/1; 132/76.4, 76.5; 29/76.1

(56) References Cited

U.S. PATENT DOCUMENTS

| | | | |
|---|---|---|---|
| 4,625,725 A | * 12/1986 | Davison et al. ............. | 128/304 |
| 4,716,894 A | 1/1988 | Lazerri et al. | |
| 4,921,493 A | * 5/1990 | Webb, Jr. et al. ............. | 606/85 |
| 4,941,246 A | * 7/1990 | Finnegan ....................... | 29/78 |
| 5,156,606 A | 10/1992 | Chin | |
| 5,601,561 A | 2/1997 | Terry et al. | |
| 5,722,977 A | 3/1998 | Wilhelmy | |
| 5,725,531 A | * 3/1998 | Shapiro ........................ | 606/85 |
| 5,797,909 A | 8/1998 | Michaelson | |
| 5,899,901 A | 5/1999 | Middleton | |
| 5,938,662 A | 8/1999 | Rinner | |
| 5,993,204 A | * 11/1999 | Stubbs .......................... | 433/1 |
| 6,120,508 A | * 9/2000 | Grunig et al. ................. | 606/85 |

OTHER PUBLICATIONS

"Anterior Lumbar Interbody Fusion" by Hammerberg, Kim W.; Lippincott, Raven Publishers Philadephia1996.
Flyer on Freeze Dried Tissue.
Brochure:Synthes Spine "The Titanium Buttress Locking Plate", Technique Guide.
Brochure:Synthes Spine "PLIF Spacer Instruments", Technique Guide.
Brochure:Synthes Spine "Surgical Technique Using FRA Spacer Instruments," Technique Guide.
Brochure, DePuy Motech Acromed, LifeNet VertiGraft Textured Allograft Bone Grafts.

* cited by examiner

*Primary Examiner*—Eduardo C. Robert
(74) *Attorney, Agent, or Firm*—Curtis L. Harrington

(57) ABSTRACT

The system and method of the invention includes surgical instrumentation to enable a spine fusion procedure to proceed more accurately, efficiently and safely by allowing precision placement of an intervertebral implant, precision preparation of the area into which the bone graft is placed, and pre-selection of a pre-specified known shape of bone graft. In the order in which they are used, improvements in a distractor, box chisel, curette, an anterior or anterolateral type intervertebral cylindrically directed or peripheral rasp, intervertebrally operated vertebral bone plate shaping rasp, or roughing combination rasp, and an intervertebral sizing tool; any combination of which may be anatomically shaped. Several embodiments of bone graft implants are disclosed including annular flat surface implants having angled surfaces, implants having line slots to help in the insertion and orientation on insertion and in registering the implant with an impactor; any combination of which may be anatomically shaped or not. Two improved impactor embodiments and an improved curette are disclosed.

39 Claims, 21 Drawing Sheets

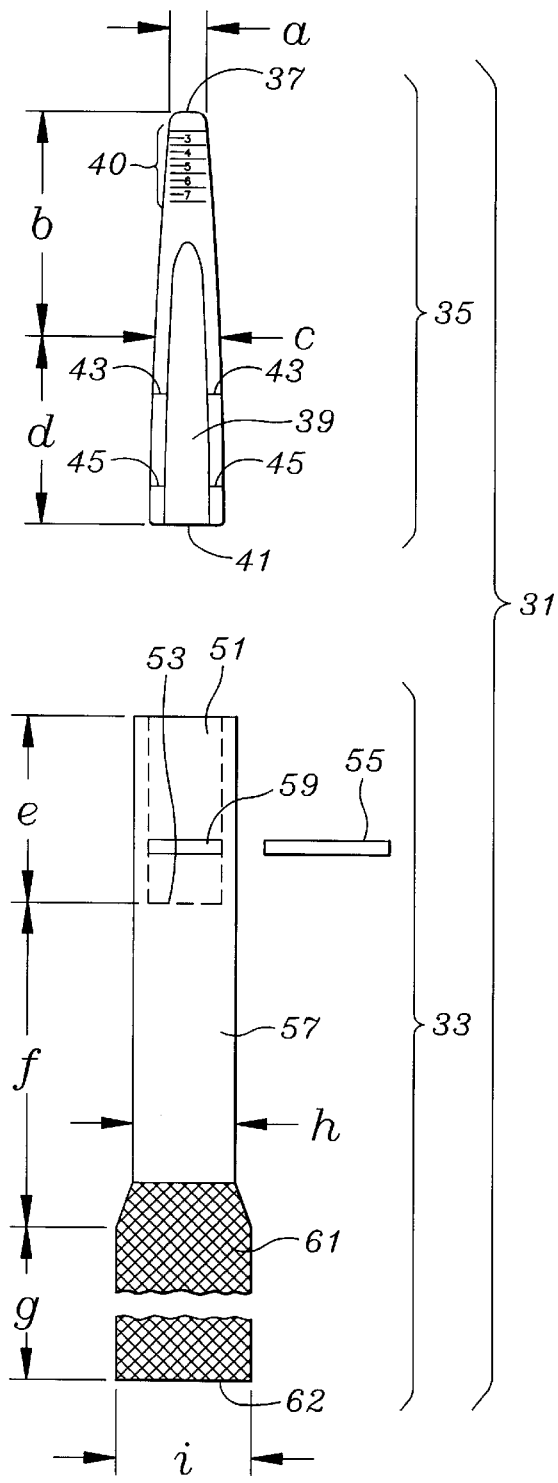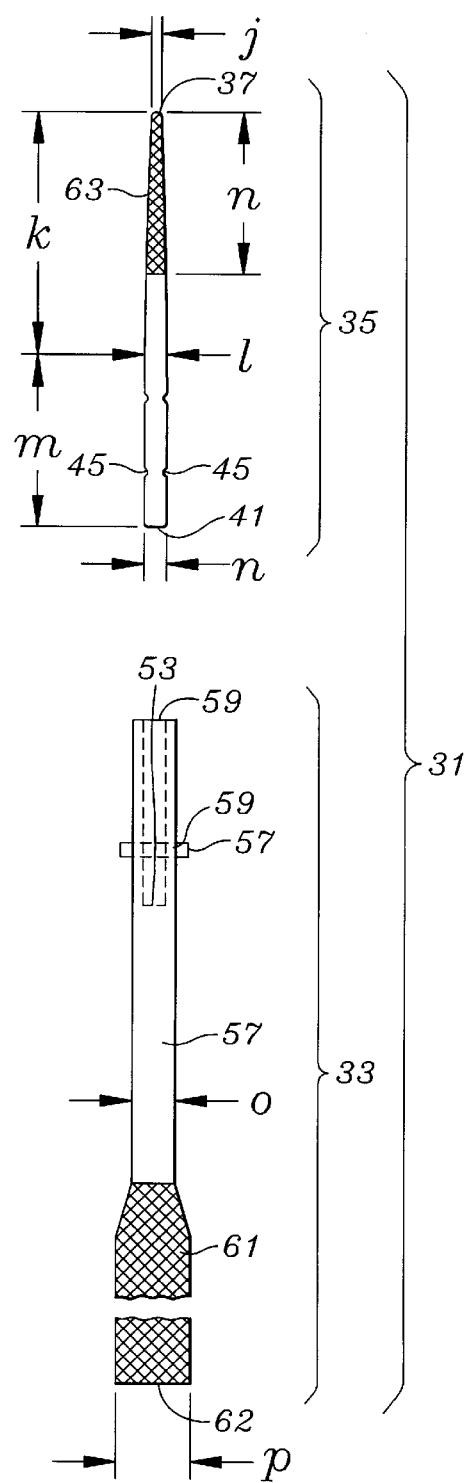

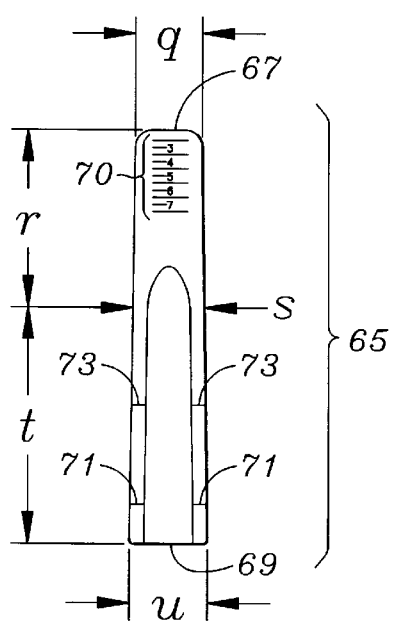
Fig. 3
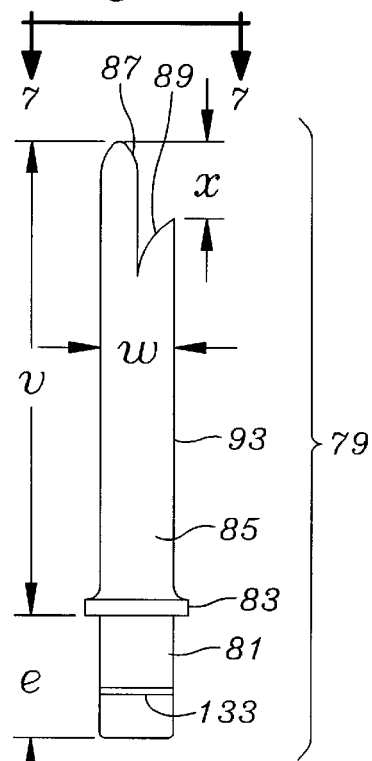
Fig. 6
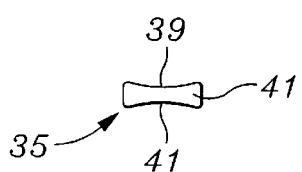
Fig. 4
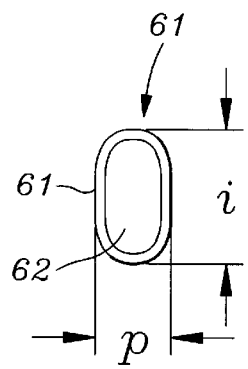
Fig. 5
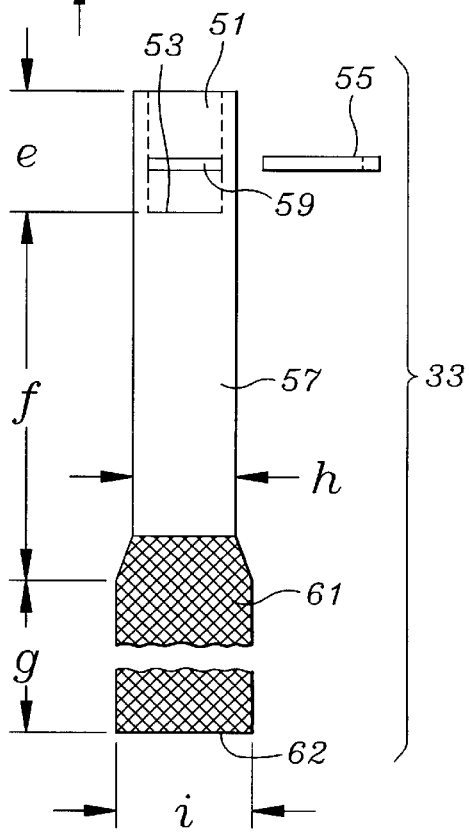

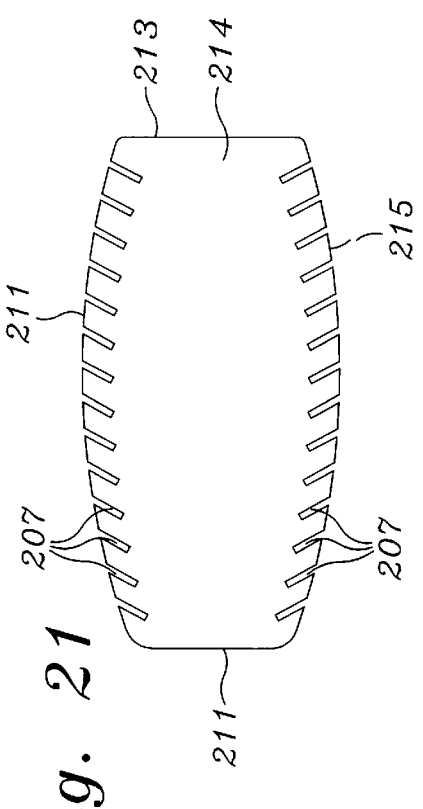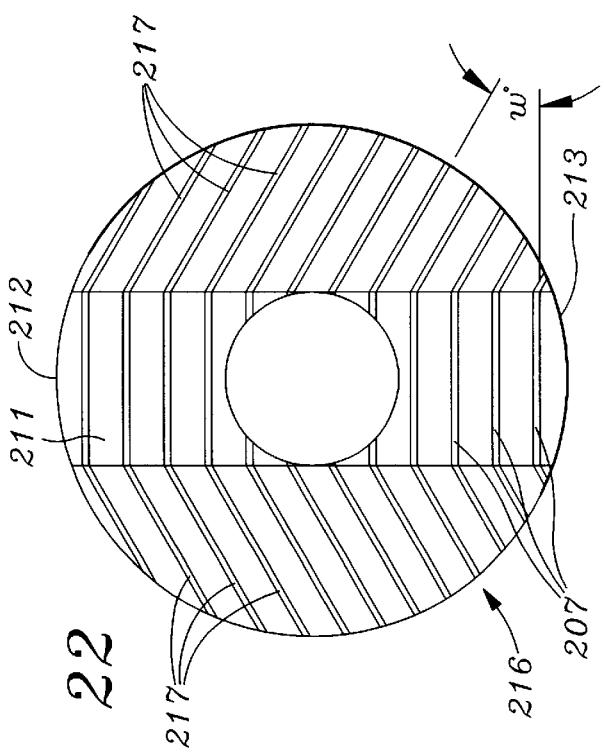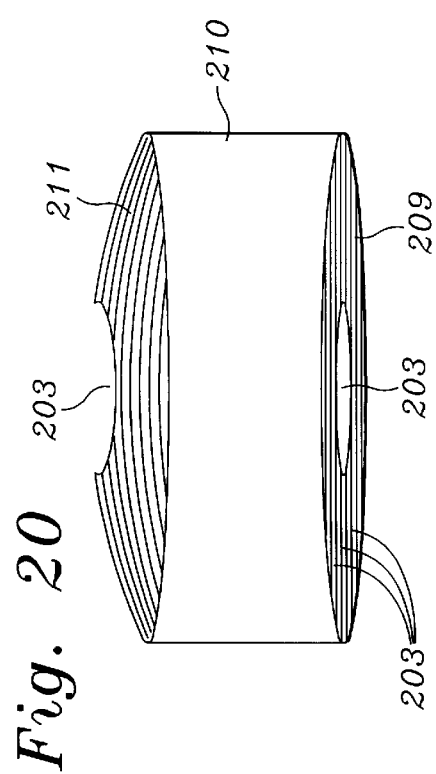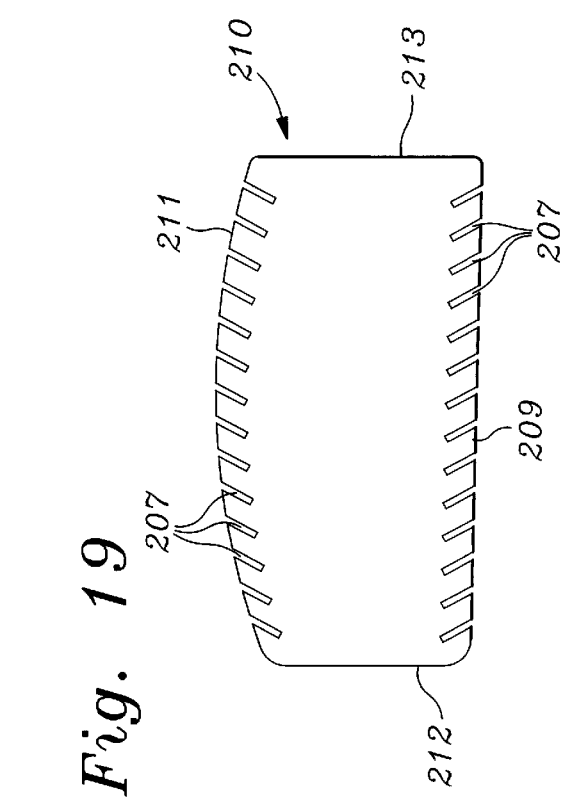

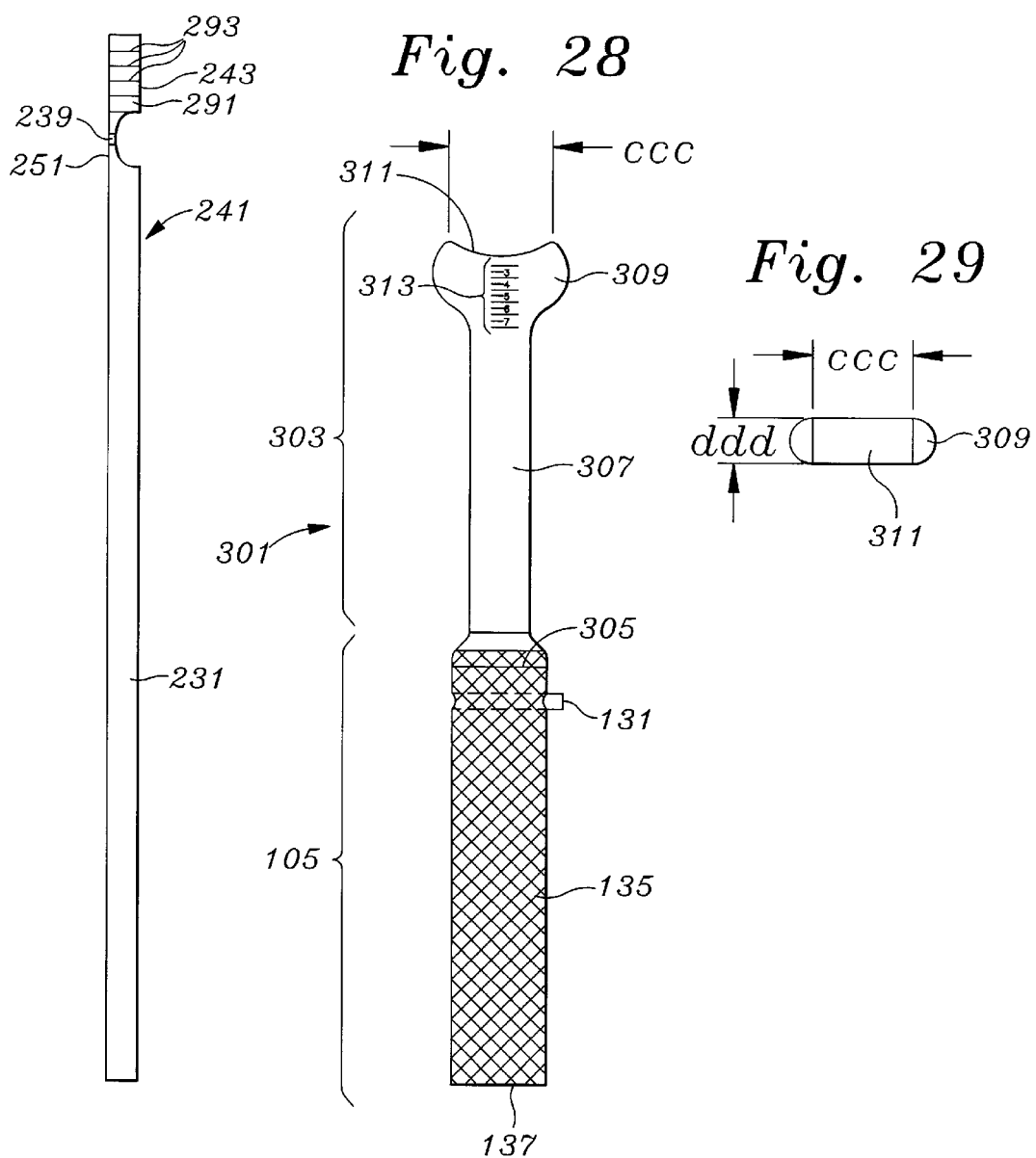

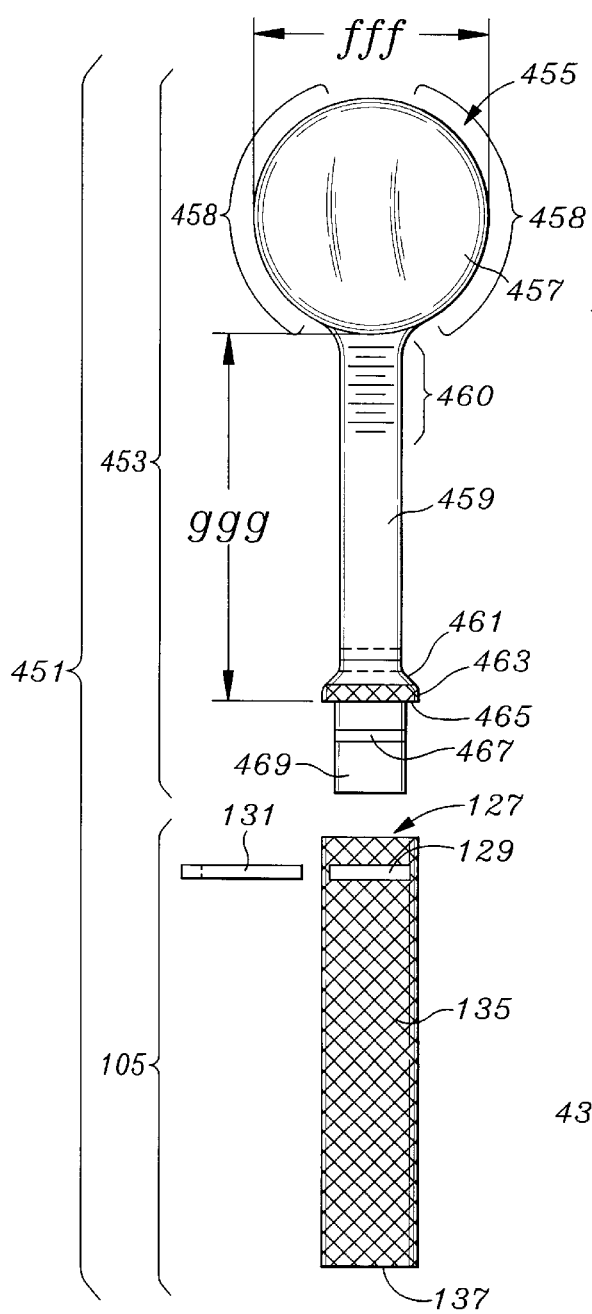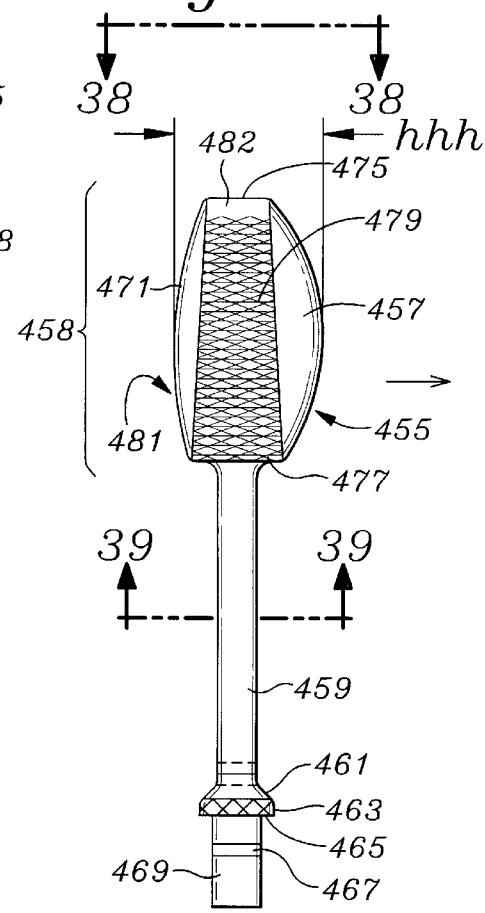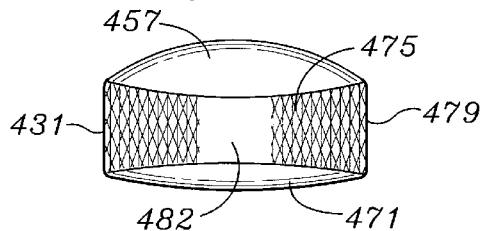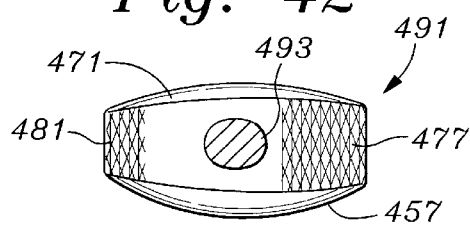

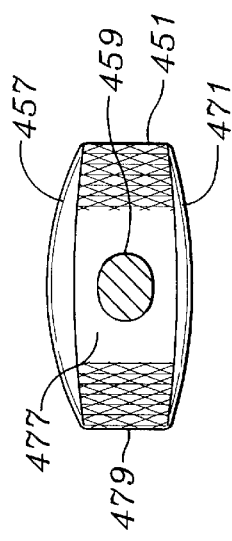
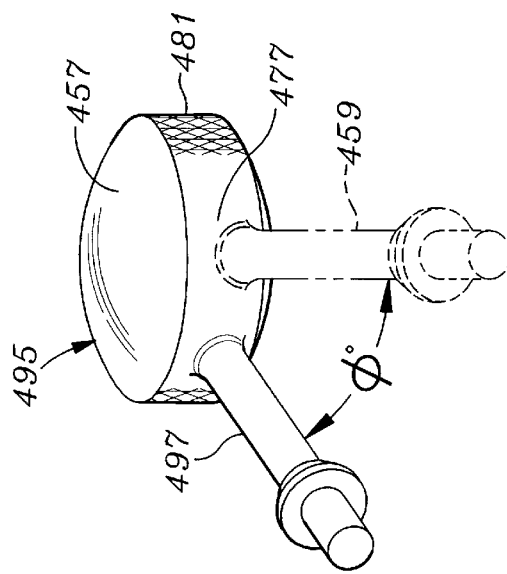
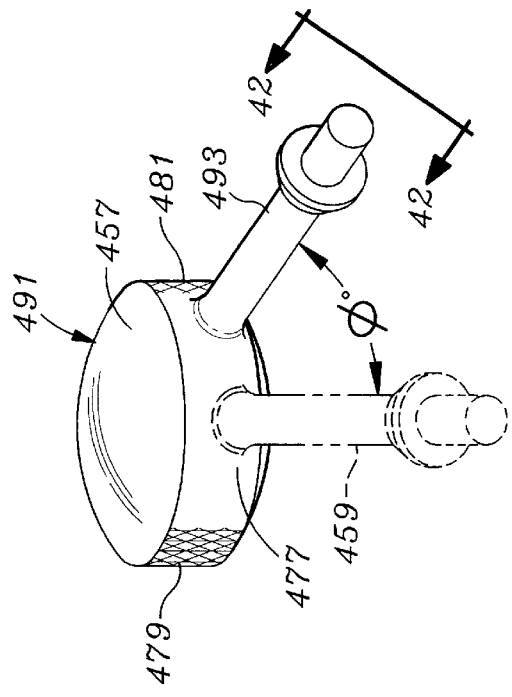

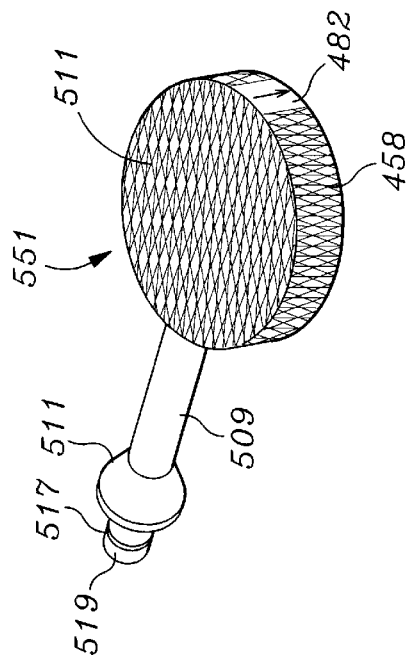
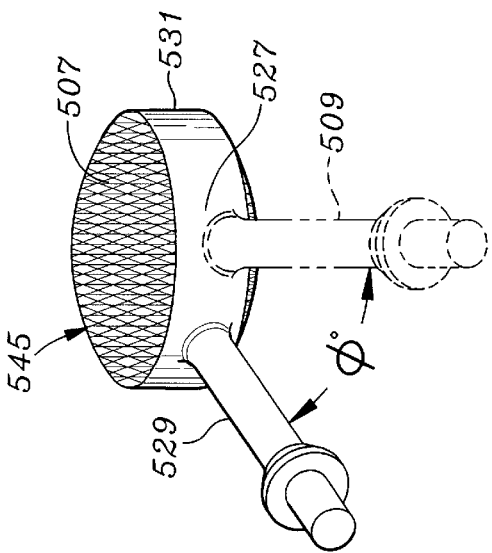
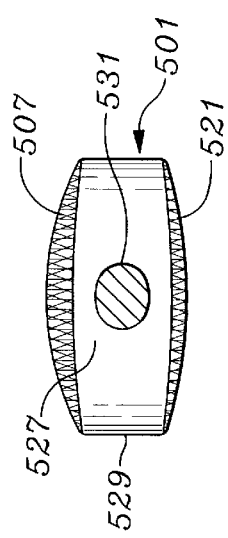
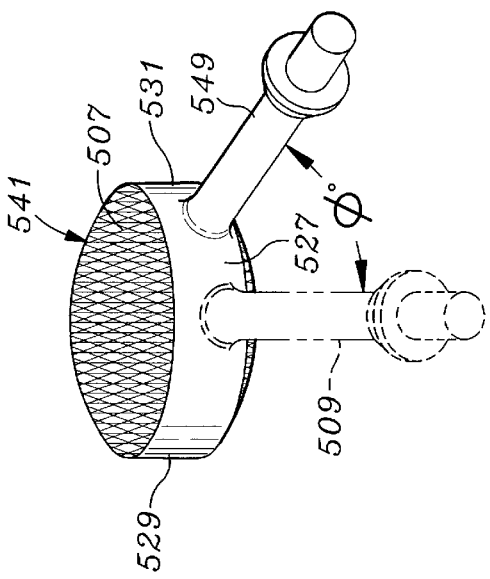

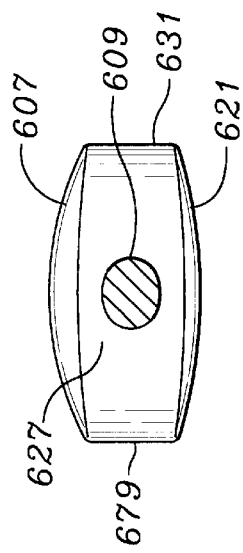
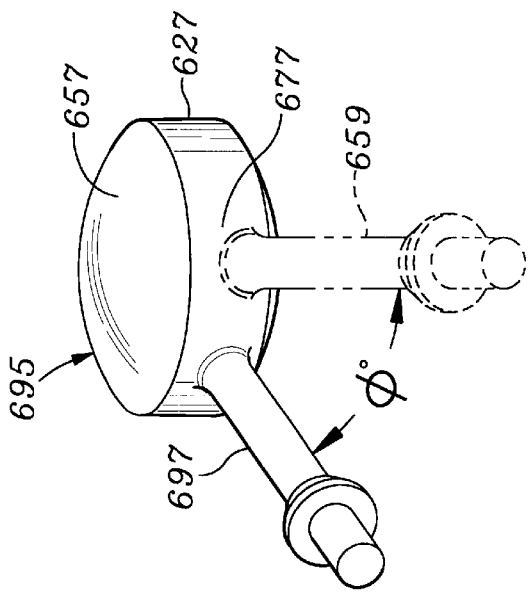
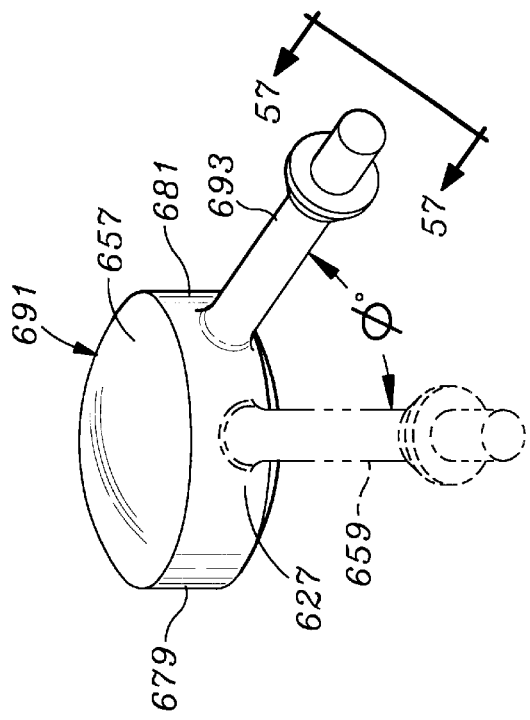

RASP FOR USE IN SPINE SURGERY

This is a continuation-in-part of U.S. patent application Ser. No. 09/416,922 filed Oct. 13, 1999.

FIELD OF THE INVENTION

The present invention relates to improvements in the field of spinal fusion to reduce the trauma and disturbance to surrounding tissues, reduce the time necessary to complete the operative procedure, increase the safety of the procedure, increase the accuracy of the procedure, provide improved instrumentation both for preparation and measurement, an improved procedure and an improved bone implant advantageously compatible with the instrumentation and procedure, both for anterior and anterolateral approaches to the spine with both open procedures as well as endoscopic procedures.

BACKGROUND OF THE INVENTION

Fusion of part of the spine for instability, infection, tumor, degeneration and deformity has become a recognized surgical procedure for spine surgeons. The three approaches to the spine to perform these procedures are anterior, posterior and lateral, with the posterior being most common. It has become increasingly recognized that fusion between two adjacent vertebral bodies in the space occupied by the disc is desirable for biomechanical, neurophysiological and anatomical reasons. This "interbody fusion" is biomechanically advantageous because the area to be fused is subjected to compressive loads rather than tensile forces as in the case for posterior element fusions. It also offers the best way to restore or maintain the opening of the neuroforamina and to restore or maintain lumbar lordosis. Quite often spinal deformity correction cannot adequately be performed without interbody surgery.

Lumbar interbody fusion is usually performed from either the anterior or posterior approaches although lateral approaches are occasionally used as well. The goals of interbody fusion are as follows: I. To maintain sagittal and frontal plane alignment of the spine, 2. To maintain or restore intervertebral space dimension, 3. To achieve a solid fusion. To this end a number of surgical techniques and graft materials have been utilized to attain a safe and successful pain relieving fusion.

Reduced to the most rudimentary level, anterior interbody fusion is performed by removing all or part of the intervertebral disc, preparing the bony interspace and placing graft material into the space. Supplemental fixation devices are often used to keep the graft from "backing out," getting crushed by the compressive and complex loads and to help maintain alignment while the fusion takes place. In prior years various bone graft materials utilized have been bovine zenograft; allograft tibia, fibula, femur, iliac crest and autograft iliac crest, and fibula. Success rates in terms of achieving fusion varied from 63–95%. They all shared the problems of graft failure from dislodgement, fragmentation, failure to achieve fusion or loss of alignment from subsidence.

More recently threaded cylindrical "cages" made from either titanium or fresh frozen allograft femoral diaphysis have been used. The stability provided by the threaded design allowed these implants to be used as a "stand alone" device not requiring further accessory stabilization. However, there have been increasing reports of non-union when initially fusion was thought to have occurred and subsidence with sinking of the implants into the vertebral body.

Threaded cylindrical cages require tapping to insert the cage. Tapping causes destruction of the supportive end plates of the vertebra allowing subsidence or "sinking in" of the implant into the body of the vertebra. This causes a loss of height of the spinal column with narrowing of the foramina and potentially compression of the exiting nerve root. There is also a flattening of the lumbar lordosis resulting in lower back pain. Furthermore the long term effects on the body from the entrapped metal implant and its local effects on the spine are unknown. If removal becomes necessary due to pain or infection the metallic cages are virtually impossible to remove without endangering the greater vessels overlying the anterior spine and necessitating massive destruction of the involved vertebrae. This creates an almost impossible situation to re-stabilize the spine. Consequently there is increasing awareness that a better design and conceived bone or non metallic biomaterials implant interbody fusion technique is necessary.

In this surgical procedure as it generally and currently is practiced, the body is entered and the spine is accessed from its anterior or lateral side. Layers of tissue surrounding the spine have to be opened carefully so that adjacent nerves and blood vessel structures, including the aorta and inferior vena cava are not ruptured and preferably are not immobilized more than necessary. Once the spine is accessed, the intervertebral disc between two adjacent vertebra must be carefully and safely removed.

A common implant used in intervertebral fusion is a femoral diaphyseal ring both freeze dried and fresh frozen allograft. This is used both for structural support to maintain the intervertebral space and to promote bone growth to fuse two adjacent vertebra together. A serious problem exists with respect to the surgical procedure of accessing, preparing the space between adjacent vertebrae, and in inserting and positioning the femoral ring allograft. One company's answer is a triple jointed spreading device. A pair of spreading levers, referred to as distractor blades, are laterally offset mounted from the centerline of the last joint of the triple jointed spreading device. The spreading levers are thin, and relatively narrow and thus potentially and actually unstable increasing the danger of inadvertent injury of surrounding tissues. The spreading device is bulky, long and since it extends straight into the space between the two vertebra, it blocks the approach and takes up valuable space and blocks needed vision into the critical operative area. The offset is for the purpose of inserting a second set of pliers-action implant holder to just clear the offset.

Unfortunately, the pliers-action implant holder must push the implant into a space which has a height taken up by the thickness of the distractor blades. This poses the danger again of dislodging the spreader device potentially causing tissue and vascular injury. Aside from the inherent instability of having spreaders, the use of the triple jointed spreading device requires excessive spreading in order to achieve its goal of providing working room to shape the interspace. Overspreading of the interspace can damage, even fracture, the vertebra. It also potentially damages the discs above and below the working level and can cause neurological injury with foraminal compression.

In some cases, a spacing tool is used or inserted while the intervertebral space is distracted with the three joint distractor. The spacing tool conventionally used is a rectangular paddle mounted at the end of a straight handle. The spacing tool is cumbersome because the handle which extends straight from the operational area further gets in the way of the surgeon. Insertion of the spacing tool is also cumbersome as it can be inserted only if the size of the inter vertebral opening exceeds the clearance size of the width of the rectangular paddle. Because the natural disc space is biconcave, the surgeon is faced with the problem of fitting a rectangular profile object into an elliptical space. This results in poor contact between the end plates of the adjacent vertebra and the surface of the bone graft which militates against successful fusion.

If the surgeon chooses to carve a rectangular space to accommodate the spacer or the graft, he must necessarily remove a great deal of the all important end plate thereby weakening the most structurally supportive part of the vertebra. This then subject the fusion site to subside and thereby resulting in unwelcome deformity with loss of normal spinal curvature and foraminal narrowing. The operation should involve only enough access to accomplish the objective of safely preparing the interspace and inserting a graft. Aspects of attaining this objective includes elimination of excessive spreading of adjacent vertebrae, enabling the surgeon to operate with as full an amount of control over the surgical field as is possible, as full an amount of vision into the surgical field as is possible, reduction of obstructions into the surgical field, and importantly, supplying the surgeon with tools which enable complete force control and selection. Proper surgical tools should lend themselves for automatic adaptation for patients of different size and of different complications. The excess force and over spacing should be eliminated.

The shape, stability, handling and force used in preparation and insertion of the implant is also a problem with spine fusion surgery. Where the implant is to be inserted, and particularly where the adjacent vertebrae are under compressive force, it may be expelled from the intervertebral space as the result of such compressive forces. The insertion using a poor grasping tool typically allows rotation or lateral displacement of the graft before the surgeon has a chance to make final placement and secure it.

The degree of spreading of two adjacent vertebrae away from the intervertebral space should be limited to avoid trauma to surrounding areas, yet enable the surgeon to access the area for removal of the disc and shaping of the interspace. Current surgical instruments available for this purpose do not enable both access, full disc removability and interspace shaping without obstructing the surgical field or unduly lengthening the time required for the procedure.

Currently used instruments to prepare the interspace such as osteotomes, chisels, curettes, rongeurs and high speed drills all have some application as well as drawbacks. The use of any combination of these instruments still does not achieve the goal of a safe, quick and anatomically shaped interspace to match a like contoured implant. Extensive use of curettes is time consuming and leaves an uneven end plate surface. Osteotomes and chisels are often too short for safe application and will not result in the ability to perform precision work. High speed drills can be quick, but can easily wrap up adjacent soft tissue resulting in catastrophic vascular injury. It is also difficult to control in the more posterior recesses of the interspace and can transgress the posterior rim and inadvertently enter the spinal canal and cause permanent neurological injury.

Another feature lacking in surgical instruments is the ability to remove instruments in a way which will not encourage side to side loosening. When an inserted instrument becomes jammed, lateral movement or force will tend to damage the surrounding areas. The surgeon's lack of control over exit angle as well as entry angle is a problem in performing this type of procedure. This is especially complicated by the fact that major blood vessels lie to either side of the operative area.

The obstruction of the surgical field is another problem. Extremely long, complicated instruments, especially those instruments which have hand engagement members located far from the surgical field, cause a significant obstruction problem. This is compounded by instrumentation which is used to hold the adjacent vertebrae apart. At the point in the procedure where the implant is to be implanted or implaced, a large number of instruments, particularly long, obstructing instruments, may be simultaneously present. The resulting obstruction is both significant and hazardous.

Implants, such as femoral diaphyseal rings currently used give the surgeon problems of (1) rotating in the interspace during insertion, (2) not remaining positioned properly to the surgical instrument utilized for implantation and fixation, (3) backing out of the interspace, (4) fracturing during insertion and (5) failure to achieve fusion.

Ideally, the implant would be contoured to restore the lumbar lordosis and match the shape of the anatomical interspace. It should have desired surface etching to securely mate to an entry instrument and resist extrusion and rotational shear forces. It should also have a surface design to increase the surface area in order to promote more rapid bone growth. No design has yet provided a solution to these problems in the allograft diaphyseal ring implant field.

What is therefore needed is a set of surgical instruments which can be utilized for spine fusion operations which reduce the visual and manual obstruction in the surgical field, give the surgeon more options for manipulation, better secure the implant on insertion and fixation, better orient the implant, enable a lesser magnitude of force to be applied to the procedure, and which enables the procedure to proceed in less time, more safely, and with better surgical control.

Other needs include anything which will reduce time during the operation, especially time spent in (1) removal of cartilage material, (2) shaping the intervertebral disc space to accept the implant, (3) selecting the correct sized implant for insertion to thus eliminate as far as possible having to remove the implant and increasing the possibility that it may be damaged from removal, or repeated re-insertions, and (4) further shaping the implant while the patient is in the midst of the operation extends the danger to the patient, the cost of operating theater time, creating the probability even in the hands of skilled surgeon that the implant may be over adjusted or improperly adjusted followed by improper implantation because no other implant was available or by wasting of a valuable implant. Not included in the list above are probabilities of having to re-set up for cartilage removal, as well as having to set up again for re-doing any porion of the operative procedure. A needed system should insure a proper fit, eliminate wasted time, and place the surgeon in a position to exert better management over the operative procedure.

SUMMARY OF THE INVENTION

The system and method of the invention includes surgical instrumentation which enables the spine fusion procedure to proceed more accurately, efficiently and safely by offering a surgical procedure for the anterior (and anterolateral) interbody approach along with new and safer instruments and custom designed implants, which allow precision placement of the graft under proper tension and in the best position to achieve spine balance and fusion. In the order in which they are used, improvements in a distractor, box chisel, curette, femoral ring implant and bone graft holder impactor will be illustrated.

A distractor includes a detachable hollow oval shaped handle and utilizing an exterior ring lock for selective engagement while providing acceptance of impact energy from the handle. The tip of the distractor is shaped for use on the flat side where necessary, but generally for use by insertion into the inter vertebral space utilizing its second greatest dimension on a gentle taper to spread adjacent vertebra. Since the spreading of the vertebra occurs primarily at the anterior side, and since spreading occurs based upon entry of the distractor, the adjacent vertebra are not over spread in order to support a shorter dimensioned spreader tool. Further, since the outer periphery of adjacent vertebra include a lip structure forming the narrowest part of the entry space, the insertion of the distender of the invention provides the least invasive method of setting the intervertebral open space, since for a given amount of spreading the distractor enters the inter vertebral space to a lesser degree than would be the case with other distraction tools. Variations include a roughening of the edge of the distractor which can wear away a slight notch in the bone to accomplish at least two objectives. The formation of a notch is advantageous because it stabilizes the resting location of the distractor, and creates fine bone fragments in the space between the vertebrae to help accelerate the fusive bone growth. More importantly, when the notches are formed upon insertion of the distractor, the distractor is stabilized both from the presence of the notches, as well as from the natural frictional fixation of the roughened edges of the distractor. The blunt end of the distractor replaces the relatively thinner, sharper end of pliers-type distractors. Preferably two sizes of distractor described herein should be included within the surgeon's available instrument set.

An advantageous box chisel is disclosed having a curved upper and lower blade which are both beveled in an direction disposed toward the centerline of the box chisel. The box chisel shape more nearly matches the intervertebral space. An open portion of the box chisel in the rear direction enables the surgeon to see whether and how much material to be removed has collected in the box chisel to enable it to be emptied. The box chisel, and other instrumentation includes a scale to give the surgeon an instant reading on the depth of penetration into the intervertebral space.

A curette is disclosed which had advantageous angling of the end portion to better enable the material in the intervertebral space to be removed.

An intervertebral space shaped rasp is provided for completing the cartilage removal process. The intervertebral rasp is available to the surgeon in a variety of sizes which enables the surgeon to either (1) quickly select the needed tool, or (2) utilize a series of such rasp tools to sequentially remove cartilage material. In either the anterior or the anterolateral procedure, the rasping action naturally occurs with a slight pivoting side to side motion of the handle about an axis through the intervertebral space. The rasp surfaces both above and below generally extend across the face of the rasp such that a pivot action about a main axis of the rasp will produce a relatively even material removal action, especially radially. The shape of the rasp not only matches generally the intervertebral space, but is shaped so as to bear slightly more axial pressure at the center of the interaxial space and slightly less at the radial outermost areas in order to take advantage of the differentially lesser rasping motion at the center. Thus for a given angle of displacement, equal material should be removed from the center and the periphery of the rasp surface. The result will be an even removal of material which will even further match the bone implants which are preferably pre-formed to a variety of sizes, but of a uniform shape within each size range.

A series of measuring gauge instruments are provided to enable the cleared intervertebral space to be probed to ascertain the correct size of implant to be utilized. Given the fact that the intervertebral space is curved and will give a different measurement depending upon where the vertical distance is measured, the introduction of a matched set of both rasps and sizers which correspond to a matched set of implants goes a long way toward both standardization of the procedure as well as creating increased safety, certainty and consistency in the vertebral implant operative procedure.

Further, the implant of the invention is pre-formed with a series of beneficial shape and structure attributes. All of the implants encompassed in the invention can be of any material ranging from human harvested allograft to modern manufactured materials. The modern manufactured materials can be of any construction and from any materials, but especially from materials having surface openings from about fifty to five hundred microns in average diameter, and a depth of from about one half to about three millimeters. The depth and opening size, stated here as an average diameter for convenience only, are for the purposes of promoting rapid, secure fusion.

In terms of its contribution to the operative system, including instrumentation as a whole, the implant is formed in sizes which preferably correspond to the gauges to facilitate quick, easy and definite selection.

Several embodiments of bone implants are disclosed including annular flat surface implants having angled surfaces, implants having line slots to help in the insertion and orientation on insertion and in registering the implant with an impactor. Where the implant is a human harvested allograft, it will have a central aperture, into which may be introduced an absorbent substrate, such as a collagen sponge, saturated with bone morphogenetic protein substance to promote even more rapid fixating bone growth. In addition, autogenous bone can be introduced, typically harvested from the iliac crest of a patient undergoing the implant procedure. Although the human harvested allograft is supplied with the a single pre-existing bore or aperture, a manufactured implant can either (1) have a series of bores into which the bone morphogenetic protien or autogenous bone can be introduced to facilitate growth, (2) have other facilitating structure into which the bone morphogenetic protien or autogenous bone can be introduced, or (3) be manufactured as an integrated structure with the into which the bone morphogenetic protien or other substance can be pre-set for timed release or for invasive displacement from the implant structure. All of the implants discussed below are considered to have these possibilities and more as technology advances.

Anterolateral implants are specially designed with surface effects which facilitate the anterolateral approach, which may typically occur at angles from about 20° to about 70° away from a straight anterior approach.

A first embodiment of an impactor includes a pair of jaws which fit loosely in an impact frame and which are held in place using a thumb adjust nut. The impact frame applies impact energy directly to the implant independently of the grasping jaws. A second embodiment of an impactor includes a pair of hinged jaws which are urged together upon withdrawal into a sleeve and which direct impact energy through the combination of an impact head of a draw bolt into a main body of the hinged jaws, along with some impact energy through the sleeve. Turning of the impact head causes the jaws to move forward in the sleeve and enables the jaws to move apart to release the implant.

BRIEF DESCRIPTION OF THE DRAWINGS

The invention, its configuration, construction, and operation will be best further described in the following detailed description, taken in conjunction with the accompanying drawings in which:

FIG. 1 illustrates a plan exploded view of a distractor utilizing a hollow balanced handle with removable end portions to help clear the surgical field even as such end portions remain in the intervertebral space to separate and stabilize adjacent vertebra, and including dimensional references;

FIG. 2, a side view of the distractor of FIG. 1 and illustrating the smaller magnitude dimension is shown;

FIG. 3 illustrates a second size and shape of a distractor tip portion as was seen in FIG. 1 is shown and has a tip portion which is less tapered than the tip portion of FIG. 1;

FIG. 4 illustrates, a bottom view, which is equivalent for both the tip portion of FIG. 1 and the tip portion of FIG. 3 is illustrated;

FIG. 5 illustrates, a butt end of the handle, which may be a universal handle illustrates its butt end which is suitable for impact energy input on insertion, and also illustrates its dimensions;

FIG. 6, a tool which may be utilized in conjunction with the distractor is seen as a notcher which has a limited penetrating round portion and an adjacent mounted blade angled to prevent over penetration of the penetrating round portion;

Referring to FIG. 19, a further embodiment of an implant is in side perspective as having a first curved surface and which also includes line slots to promote insertion, and to provide anterior support;

Referring to FIG. 20, a view of a further embodiment of the implant of the invention looking into the posterior end is seen;

Referring to FIG. 21 a side view of a further embodiment of the implant having both a first and second curved surfaces;

Referring to FIG. 22, a further variation of implant is seen having a set of linear line slots extending along a central corridor on the first curved surface of the implant and flanked by two series of line slots which are oriented at an angle with respect to the linear extent of the line slots in the central corridor;

Referring to FIG. 26, a single one of the lever jaw combinations shown in FIGS. 23–25 are shown without its opposite lever jaw combination in order to show a face of the jaw member;

Referring to FIG. 27, an implant is pictured having a first array of line slots having a first spacing over a first portion of the surface of an implant and a second array of line slots which are much more closely spaced over a second portion of the surface of the implant;

Referring to FIG. 28, a completion impactor is seen, including an extension fore end section which fits into a handle portion seen in FIG. 8;

Referring to FIG. 29, an end view of the radiused end of the impactor of FIG. 28 is seen;

FIG. 35 is a plan view of an anterior type intervertebral cylindrically directed or peripheral rasp fitting the intervertebral area for safely removing material in a generally posterior direction and which will reduce time and enhance safety for cartilage removal;

FIG. 36 is an end view of the handle of the rasp of FIG. 35;

FIG. 37 is a side view of the intervertebral cylindrically directed or peripheral rasp of FIG. 35 and illustrating the different curvature of the two sides facing the bone plates of the spine;

FIG. 38 is an end view of the intervertebral cylindrically directed or peripheral rasp at a side opposite the shaft;

FIG. 39 is an end view of the intervertebral cylindrically directed or peripheral rasp at the shaft;

FIG. 40 is a perspective view of a left approach anterolateral procedure peripheral rasp;

FIG. 41 is a perspective view of a right approach anterolateral procedure peripheral rasp;

FIG. 42 is an end view of the left approach anterolateral procedure peripheral rasp looking into the shaft;

FIG. 46 is an end view of the intervertebrally operated vertebral bone plate shaping rasp at the shaft;

FIG. 47 is a perspective view of a left approach anterolateral procedure bone plate shaping rasp;

FIG. 48 is a perspective view of a right approach anterolateral procedure bone plate shaping rasp;

FIG. 50 is a perspective view of a roughing combination rasp which combines the cylindrically peripheral directed rasping surfaces with the face shaping rasping surfaces of the bone plate shaping rasp and which may be advantageously employed for initial shaping to finishing depending upon the coarseness of the rasp surface;

FIG. 54 is an end view of the anatomically shaped intervertebral sizing tool at the shaft;

FIG. 55 is a perspective view of a left approach anterolateral procedure anatomically shaped intervertebral sizing tool;

FIG. 56 is a perspective view of a right approach anterolateral procedure anatomically shaped intervertebral sizing tool;

DETAILED DESCRIPTION OF THE PREFERRED EMBODIMENT

Figure 9:
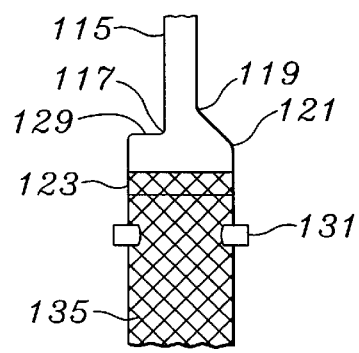
Referring to FIG. 9, a side view taken along line 9—9 near the junction of the assembled chisel insert portion and handle portion gives a clearer view of the reverse impact groove.

The description and operation of the contained direct particle beam flow abrasion system of the present invention will be best described with reference to FIG. 1. FIG. 1 illustrates a plan exploded view of a distractor 31 of the invention as a two-piece instrument including a handle portion 33 and a tip portion 35. Dimensional markers are illustrated to correspond with one set of dimensions which have been found to be advantageous. Distractor 31 has an end 37 which has a gentle transition from sides to end 37 and has a dimensional width at the end represented by the letter "a" of about eight millimeters. The distance over which the width changes gives an idea of slope without limitation to a linear edge. A dimension "b" is preferably about twenty-five millimeters over which the width of the tip portion increases to a dimension "c" of about thirteen millimeters. This gives an aspect ratio change of the width of the tip portion 35 of five millimeters change over twenty-five millimeters or about 5/25, or about 0.2. The remaining length of the tip portion 35 is set forth as dimension "d" which may preferably be about sixty-five millimeters.

The tip portion 35 also includes a shallow depression 39 which provides a little additional clearance for inserting a femoral ring implant and associated holder at the side, and can also provide additional complementary matching with the handle portion 33. A scale 40 provides depth information to the surgeon indicating the extent of penetration from the end 37 of the tip portion 35. As can be seen, the shallow depression 39 extends over about half of the dimension "b". The shallow depression 39 extends to a lower end 41 of the tip portion 35. A pair of locking slots 43 and 45 extend across the width of handle portion not occupied by the shallow depression 39. Limitation of the lengths of the locking slots 43 and 45 facilitates disengagement of the tip portion 35 from the handle portion 33 by limiting the engagement holding force.

Handle portion 33 includes an upper blind bore 51 which is complementary to lower end 41 of the tip end 41 of the distractor 31, and may optionally be complementary to the shallow depression 39. A terminal surface 53 provides a wide surface of contact to the lower end 41 of the tip end 35. A locking ring 55, shown in exploded fashion just to one side of handle portion 33, fits around an outside shaft 57 of the handle portion 33 and into a slot 59 which enables the locking ring 55 to fit within the locking slots 45. The external locking ring 55 arrangement enables a locking mechanism which is compatible with and capable of surviving high temperature sterilization.

Outside shaft 57 may preferably be oval to more efficiently accommodate the tip portion 35. Below the outside shaft 57, a burled handle 61 with butt end 62 is shown in broken format to facilitate illustration of details elsewhere on the distractor. With regard to the handle portion 33, the length of upper blind bore 51 dimension "e" is preferably about forty millimeters. The dimension "f" between the level of the terminal surface 53 and the larger dimension of the oval burled handle 61 is preferably about 60 millimeters. The oval burled handled 61 preferably has a dimension "g" of about 200 millimeters in length. The width of the larger dimension of the outside shaft 57 has a dimension "h" of about twenty-five millimeters, while the width of the wider dimension of the oval burled handle 61 has a dimension "I" of about thirty five millimeters. The tip portion 35 fits within the upper blind bore 51 with the locking slot 45 engaging the locking ring 55 to form an integrated distractor. The tip end 37 can be inserted between two vertebrae, and once in place, the handle portion 33 can be removed to leave the operating theater unobstructed.

Referring to FIG. 2, a side view of the distractor 31 of FIG. 1 is seen. A smaller magnitude dimension is illustrated, at the tip portion 35 due to the overall plank shape, and at the handle portion 33 due to the oval shape. From the tip 37, dimension "j" is about three millimeters. At a distance of dimension "k" of about fifty millimeters away from tip 37, the width dimension "l" seen in FIG. 2 is about five millimeters, both at the distance of dimension "k", and at the lower end 41. This gives an aspect ratio change, over the most narrow dimension of the tip portion 35 of about two millimeters change over twenty-five millimeters or about ²⁄₂₅, or about 0.08. As an alternative, at the tip 37, dimension "j" can be about two millimeters. At a distance of dimension "k" of about twenty five millimeters away from tip 37, the width dimension "l" seen in FIG. 2 can still be about five millimeters, both at the distance of dimension "k", and at the lower end 41. This gives an aspect ratio change, over the most narrow dimension of the tip portion 35 of about three millimeters change over twenty-five millimeters or about ³⁄₂₅, or about 0.12. The dimensions "j", "k", & "l" give an idea of the slope and angle of the upper portion of the tip portion 35.

Dimension "m" is about forty millimeters. Also more fully seen from a side view are the pair of locking slots 43 and 45. An upper end of tip portion 35, over a distance of magnitude "n" of about twenty five millimeters includes a rasp, file like, or burled or rasp surface 63 is seen. This roughened surface helps to notch the edges of adjacent vertebrae when the distractor 31 is inserted, as well as stabilize the distractor 31 tip portion 35 in the operative field.

The handle portion 33 has an outside shaft 57 width dimension "o" of about 10 millimeters. The width of the burled handle 61 is a dimension "p" of about 15 millimeters.

Referring to FIG. 3, a second size of a distractor 31 tip portion 65 is shown. The tip portion 65 is less tapered than the tip portion 35, and has a wider end 67. The width of the end has a dimension represented by the letter "q" of about thirteen millimeters. The distance over which the width changes gives an idea of slope without limitation to a linear edge. A dimension "r" is preferably about twenty-five millimeters over which the width of the tip portion 65 increases to a dimension "s" of about fifteen millimeters. This gives an aspect ratio change of two millimeters change over twenty-five millimeters or about ²⁄₂₅, or about 0.08. The remaining length of the tip portion 35 is set forth as dimension "t" which may preferably be about sixty-five millimeters. The width of a lower end 69 is a dimension "u", which is preferably about seventeen millimeters. Tip portion 65 also has locking slots shown as locking slots 71 and 73. A side view of tip portion 65 is equivalent to the side view of tip portion 65 seen in FIG. 2.

Referring to FIG. 4 a bottom view, which is equivalent for both the tip portion 35 and tip portion 65 is illustrated and discussed as a tip portion 35. Shallow depression 39 is seen, as is the lower end 41.

Referring to FIG. 5 a butt end of the handle 61 showing butt end 62, suitable for impact energy input on insertion, also illustrates the dimensions "p" and "I". The distractor 31 handle portion total length is about 300 millimeters. As is seen in FIG. 5 an optional bore 77 is shown open at butt end 62. This is but one method to hollow out the handle portion 33 to lighten its weight and to provide an overall balanced distractor 31. Other methods may be used, such as providing a step instead of terminal surface 53 and extending a smaller bore completely through the handle portion 33.

Referring to FIG. 6, a tool which may be utilized in conjunction with the distractor 31 is seen as a notcher 79. Notcher 79 can fit within handle portion 33 or possibly any other handle portion in the later Figures. It is shown in exploded view above handle portion 33 which will not be further mentioned with respect to the notcher 79. Notcher 79 has an insertion member 81 below a stabilization neck 83. An extension 85 continues from the stabilization neck 83 on one side to an upper round extended terminal end 87 which is the portion inserted into the intervertebral disc space. On the other side, extension 85 continues from the stabilization neck 83 to an angled blade 89. Angled blade 89 is separated from the upper round extended terminal end 87 by a deep rounded notch 91. From a point above the angled blade 89, and extending rearwardly on the notcher 79, a flat rail 93 may be provided to lend strength to the extension 85 and to help limit entry of the blade 89 into the intervertebral disc space.

The dimensions of the notcher 79 include a working length, not including the handle portion 33, shown by dimension "v" as preferably about twelve and a half centimeters. The width between the bottom of the upper round extended terminal end 87 and the outermost portion of the blade 89 is shown to be a dimension "w" which is preferably about ten millimeters. As before, the length of the insertion member 81 has a dimension "e" which matches dimension "e" of the handle portion 33. The distance from the tip of blade 89 along the longitudinal distance of the notcher 79 to the end of upper round extended terminal end 87 is shown as a dimension "x" of about ten centimeters.

Figure 7:
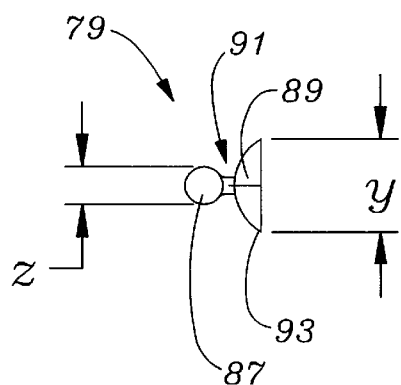
FIG. 7, an end view taken along line 7—7 of FIG. 6 shows the rounded extent of the extension and the shape of the upper round extended terminal end along the length of the extension 85.

Referring to FIG. 7, an end view taken along line 7—7 of FIG. 6 shows the rounded extent of the extension 85 and the shape of the upper round extended terminal end 87 along the length of the extension 85. The width of the flat rail 93 is represented by the dimension "y" of about ten millimeters. The width of the upper round extended terminal end 87, which is somewhat dominated by a circular shape, is a width shown as "z" of about six millimeters.

Figure 8:
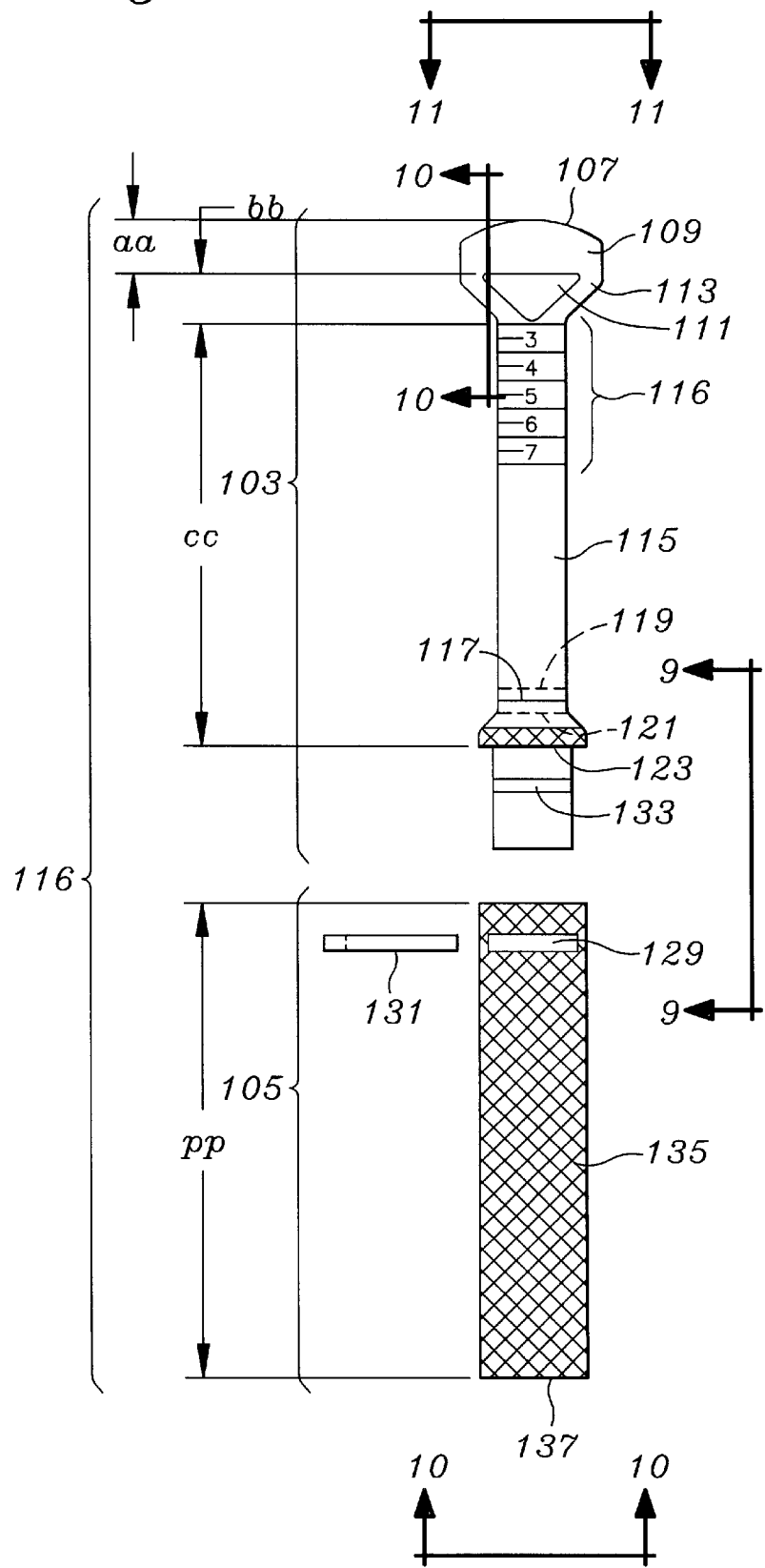
FIG. 8, a top plan view of a box chisel includes a chisel insert portion and a handle portion, the insert portion having a curved end which is the tip end of a double blade longer dimension of the box cutting portion and includes an inwardly directed bevel.

Referring to FIG. 8, a top plan view of a box chisel 101 is seen. Box chisel 101 includes a chisel insert portion 103 and a handle portion 105. At the top of the chisel insert portion 103 is a curved end 107 which is the tip end of a double blade longer dimension of the box cutting portion 109 and including an inwardly directed bevel (not seen in FIG. 8). A through opening 111 is in communication with the box cutting portion 109 and facilitates cleaning of the chisel insert portion 103 and gives the surgeon a greater view into the contents of the box cutting portion 109. The box cutting portion 109 is connected by a pair of side supports 113 to a chisel insert portion 103 shaft 115, which may preferably have a flattened surface in its greater lateral dimension on at least the top side, and flattened in its smaller lateral dimension at the sides. Shaft 115 also preferably has a scale 116 which illustrates the distance from any point on the shaft 115 to the maximum linear extent (at the middle as shown in FIG. 8) of the curved end 107. The numbering of the scale 116 will be discussed with regard to the linear dimensioning of the box chisel 101.

At the end of chisel insert portion 103 nearest its connection to handle portion 105, a solid line reverse impact groove 117 is preferably a right angled ledge which can engage an impacting tool to reverse the chisel insert portion 103 from its engagement into the inter vertebral area. The force expected to be required for reversal is slight and thus the height and impact area of the groove 117 may be slight. Also seen in dashed line format are transition lines 119 and 121 which reflect changes in the angularity of the rear of the chisel insert portion 103. Just below the groove 117, a smooth portion of the shaft 115 leads to an abbreviated length burled portion 123. Below the burled portion 123, a stepped inward insertion member 125. Insertion member 125 fits into an bore 127 at the top of the handle portion 105. Handle portion 105 includes an open slot 129 for accommodating a locking ring 131 to enable locking ring 131 to engage a groove 133 which extends laterally across the insertion member 125 to enable the chisel insert portion 103 to be snap locked within the handle portion 105. Handle portion 105 also includes a burled surface 135 below the open slot 129, and extending to a butt end 137.

The linear dimensioning of the box chisel 101 begins with the length from the longest extent of the curved end 107. The length from the end of curved end 107 to the beginning of the through opening 111 is a magnitude indicated as "aa" and is preferably 1.5 centimeters. The distance along the chisel insert portion 103 across the through opening 111 is a distance "bb" and preferably about 1.0 centimeters. The scale 116 begins where the through opening 111 ends, which is about 2.5 centimeters from the end of curved end 107. Thus the first scale line just at the through opening 111 is 2.5 centimeters. The next scale line extends partially across the width of shaft 115 and shows a "3", indicating 3 centimeters. The scale continues with whole lines and partial lines and shows a depth of up to 7.5 centimeters.

The remaining dimensions of the box chisel 101 are seen at dimension "cc" of about thirteen centimeters, which is the length from the bottom of the burled portion 129 of the chisel insert portion 103 to the beginning of the through opening 111. Dimension "dd", which is preferably about 4.0 centimeters, extends from the bottom of the burled portion 129 to the end of the stepped inward insertion member 125. The length of handle portion 105 has a dimension "ee" which is preferably about eighteen centimeters. The bore 127 will be deep enough to accommodate the stepped inward insertion member 125, and need not have a stepped internal surface in order to limit travel of the stepped inward insertion member 125. Handle portion 105 butt end 137 may be open and show a hollow through bore for weight reduction and balance purposes, or preferably bore 127 will be a blind bore significantly exceeding the length of stepped inward insertion member 125, but stopping short of the butt end 137, in order to lighten and balance the handle portion 105.

Referring to FIG. 9, a side view taken along line 9—9 near the junction of the assembled chisel insert portion 103 and handle portion 105 give a clearer view of the reverse impact groove 117 is seen. The reverse impact groove 117 is a right angled corner at the junction of a flat shaft 115 and an impact surface 139. Flat shaft 115 surface aids in the use of a reverse impact tool against the impact surface 139. Also seen is the locking ring 131 hugging the main body of the handle portion at the open slot 129. An additional slot opposite slot 129 may be provided for double engagement of the chisel insert portion 103.

Figure 10:
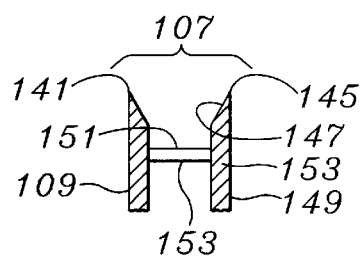
Referring to FIG. 10, a side view looking into the box cutting portion illustrates first and second edges each also having a bevel.

Referring to FIG. 10, a side view looking into the box cutting portion 109 illustrates an first edge 141 having a bevel 143 and a second edge 145 having a bevel 147. Because the drawing of FIG. 10 is a sectional view, the curved nature of the edges 141 and 143 beyond the section line are not illustrated. The bevels 143 and 147 face each other as the bevels 143 and 147 are faced inward with respect to box cutting portion 109. A side wall 149 is seen having a side edge 151 which may also contain a bevel 153 facing into the box cutting portion 109, seen because of the sectional view shown.

Figure 11:
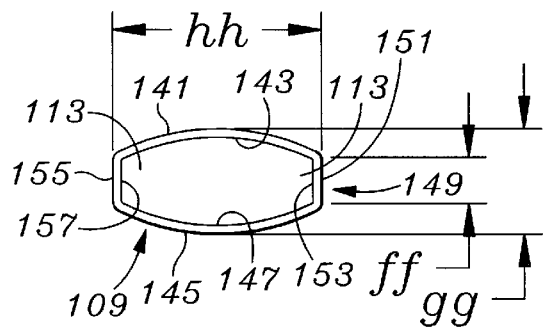
Referring to FIG. 11, a view looking into the end of the box cutting portion is seen.

Referring to FIG. 11, a view looking into the end of the box cutting portion 109 is seen. Also seen into the space within the box cutting portion 109 are the side supports 113. First edge 141 is seen immediately adjacent its bevel 143, and second edge 145 is seen immediately adjacent its bevel 147. Side wall 149 is indicated in the vicinity of edge 151. Edge 151 has an adjacent bevel 153, while edge 155 is seen as having an adjacent bevel 157. As can be seen from FIG. 10, all of the bevels or bevel surfaces 143, 147, 153, and 155 are inwardly directed. This technique maximizes the cartilage material which will be removed on entry of the box chisel 101, even though some compression of the material occurs by virtue of the bevel surfaces 143, 147, 153, and 155. This means that less time will need to be taken in individually and carefully removing more of the material which would otherwise be present without the ability to remove material at the outermost periphery of the edges 101, 145, 151 and 155. Another milestone of efficiency is achieved by virtue of the fact that the edges 141 and 145 are curved to form the curved end 107. The vertebrae support areas to be excised of cartilage are rounded, particularly the portion most closely adjacent the spinal chord. The commonly available box chisels which have straight edges require the surgeon to spend additional time removing cartilage material from the back of the inter vertebral space, in an inexact, manual fashion. Elimination of this step not only saves time, it reduces the risk of surgery by eliminating the chance for a manual error in removing material in an inexact manner.

The dimensions of the chisel 101, and particularly the dimensions of the box cutting portion 109 are illustratable with respect to FIG. 11. There are two preferable sizes for the chisel insert portion 103 with reference to the overall width.

For the thirty-two millimeter size of the chisel insert portion, the minimum width of the narrow edge or that of the side wall 149 is indicated by a dimension "ff" which is preferably about eight millimeters. The maximum width of the narrow edge of the box portion 109 at its center is indicated by a dimension "gg" which is preferably about sixteen millimeters. The width of the box portion 109, between edge 151 and edge 155 is indicated by a dimension "hh" which is preferably about thirty-two millimeters.

For the twenty-eight millimeter size of the chisel insert portion, the minimum width of the narrow edge or that of the side wall 149 is indicated by a dimension "ff" which is preferably about six millimeters. The maximum width of the narrow edge of the box portion 109 at its center is indicated by a dimension "gg" which is preferably about fourteen millimeters. The width of the box portion 109, between edge 151 and edge 155 is indicated by a dimension "hh" which is preferably about twenty-eight millimeters, which defines the size of the twenty-eight millimeter size of the chisel insert portion 103.

Figure 12:
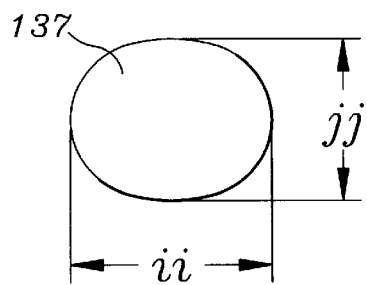
Referring to FIG. 12, an end view of the butt end of the handle portion enables illustration of the square oval shape.

Referring to FIG. 12, an end view of the butt end 137 of the handle portion 105 enables illustration of the square oval shape. The handle portion 105 has a maximum lateral dimension represented by dimension "ii" of about three centimeters. The handle portion 105 has a minimum lateral dimension represented by dimension "jj" of about two and a half centimeters. All of the oval shapes for all of the instruments can be elliptical ovals or square ovals or even rounded edge rectangular shapes, as well as any variation therebetween.

Figure 13:
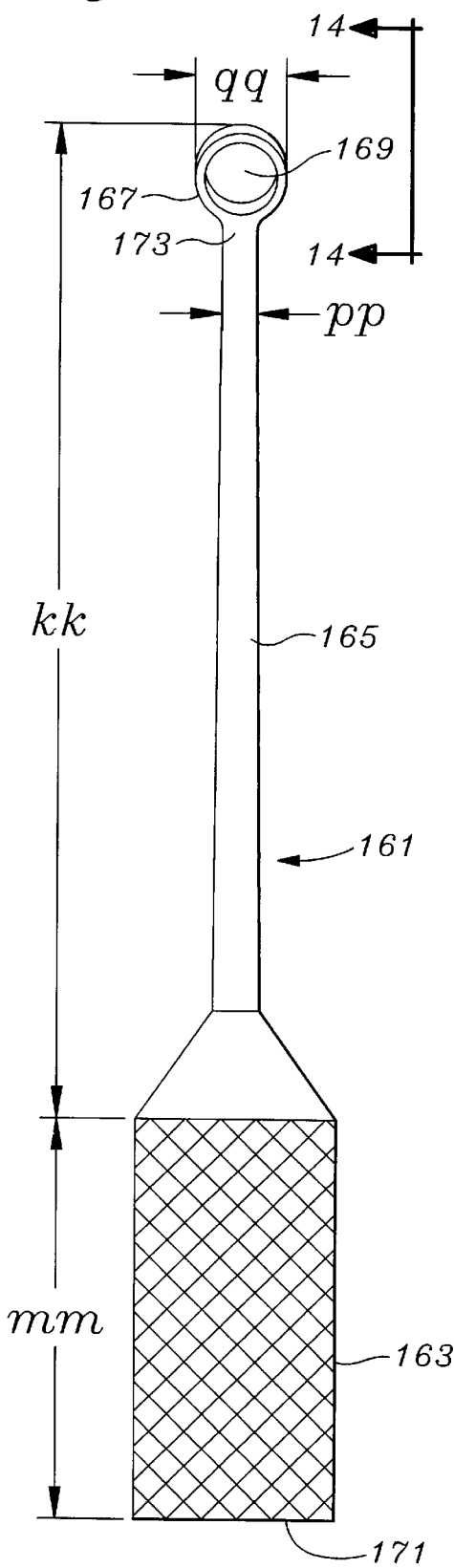
Referring to FIG. 13, a plan view of a curette is seen which has advantages in the performance of the fusion operative procedure.

Referring to FIG. 13, a plan view of a curette 161 is seen which has advantages in the performance of the fusion operative procedure. A burled handle 163 can be round or oval and includes a relatively straight shaft 165 having an extremely thin cutting ring structure 167 at the end of straight shaft 165. Note that the shaft 165 is not angled to form a short length of angled shaft before engagement of the cutting ring structure 167. This arrangement enables the curette 161 to be inserted into the intervertebral area more advantageously without having the working angle dictated by an angular bend, which occurs in conventional curettes, in the shaft 165 in advance of the cutting ring structure. Shaft 165 can also be tapered. Because FIG. 11 is a plan view with respect to the overall length of the curette 161, a thin cutting ring structure 167 has a through opening 169 which appears non round, although this is not the case.

The distance between the end of extremely thin cutting ring structure 167 and the upper part of the handle 153 is represented by the magnitude "kk" and is preferably about fifteen centimeters. The distance between the upper part of the handle 163 and butt end 171 of the handle 163 is represented by the magnitude "mm" and is preferably about fifteen centimeters, to give an overall length of the curette 161 of about 30 centimeters. The width of the shaft 165 close to the handle 163, but before transitioning into the handle is a magnitude "oo" and is preferably about eight millimeters. The most slender portion of the shaft is at or near a neck 173 at the transition to the extremely thin cutting ring structure 167 and has a magnitude "pp" and is preferably about four millimeters.

The width of the extremely thin cutting ring structure 167 is virtually a radius measurement due to the thinness of the material and represented by the magnitude "qq" and is preferably about one centimeter.

Figure 14:
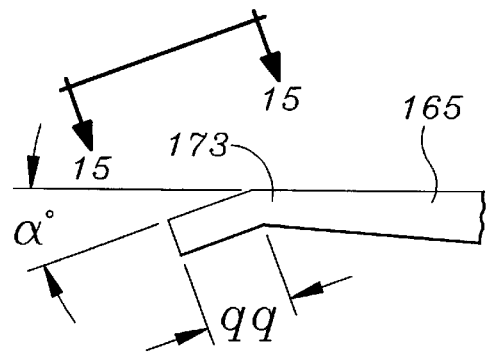
Referring to FIG. 14, a view taken along line 14—14 of FIG. 13 illustrates the angularity of extremely thin cutting ring structure with regard to the general linear extent of the shaft.
Figure 15:
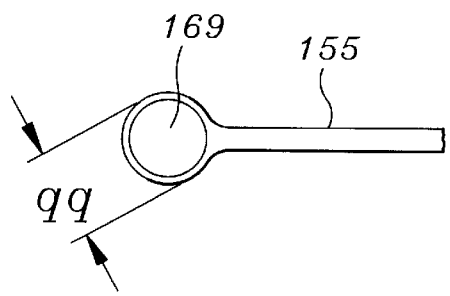
FIG. 15 is a view taken along line 15—15 of FIG. 14.

Referring to FIG. 14, a view taken along line 14—14 of FIG. 13 illustrates the angularity of extremely thin cutting ring structure 167 with regard to the general linear extent of the shaft 165. The extremely thin cutting ring structure 167 lies in a plane which is angled at an angle α with respect to the linear extent of shaft 165 which is preferably about 15° but may be supplied in a range of angularity of from about 10° to about 20°. Referring to FIG. 15, a view taken along line 15—15 of FIG. 14 is a view taken along the axis of the through opening 169. Other structure is illustrated in accord with the earlier Figures for completeness. In the operative procedure, after the box chisel 101 is utilized, the curette 161 is used to remove any cartilage tissue not removed by box chisel 101.

Once this part of the procedure is completed, an implant such as a femoral implant is to be inserted into the space between the vertebrae. Most of the prepared rings currently available have a surface area which is modified by dimpling or forming so that dimples protrude away from the ring. This technique only reduces the frictional contact area with which the vertebrae bone surface can contact the femoral ring implant. Reduced frictional contact increases the likelihood of the bone slipping out of the intervertebral space. This likelihood is sufficiently probable that a vertebral buttress locking plate has been developed as a plate which is secured to the anterior side of a vertebra and which extends about half way across the intervertebral space specifically to hold the femoral ring implant in place. The dangers and side effects from introducing metal into the body are significant. The fact that such a device is considered indicates that femoral ring bone type implant fixation is a significant problem.

Figure 16:
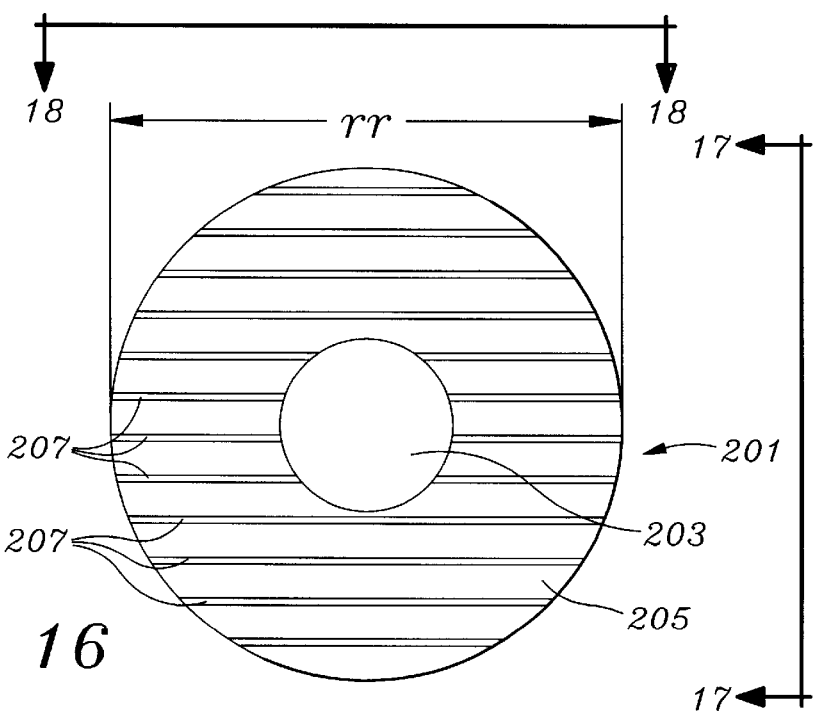
Referring to FIG. 16, a top view of a femoral ring bone implant preferably harvested from the femur of a human, and then sterilized and treated to be used to encourage bone growth in any bone tissue contacting the implant.

Referring to FIG. 16, a top view of a femoral ring bone implant 201 is seen. Implant 201 was preferably harvested from the femur of a human, and then sterilized and treated to be used to encourage bone growth in any bone tissue contacting the implant 201. Implant 201 is an annular ring, and may also have a central aperture 203. A central aperture 203 is not likely where the implant 201 is not manufactured from material harvested from humans to accommodate augogenous gone graft or other osteogenetic and osteoinductive materials. An upper surface 205 includes a series of possibly evenly spaced line slots 207. Line slots 207 are channels cut into the implant 201. The general diameter of the implant 201 has a magnitude "rr" of from about twenty-five to about thirty millimeters.

Figure 17:
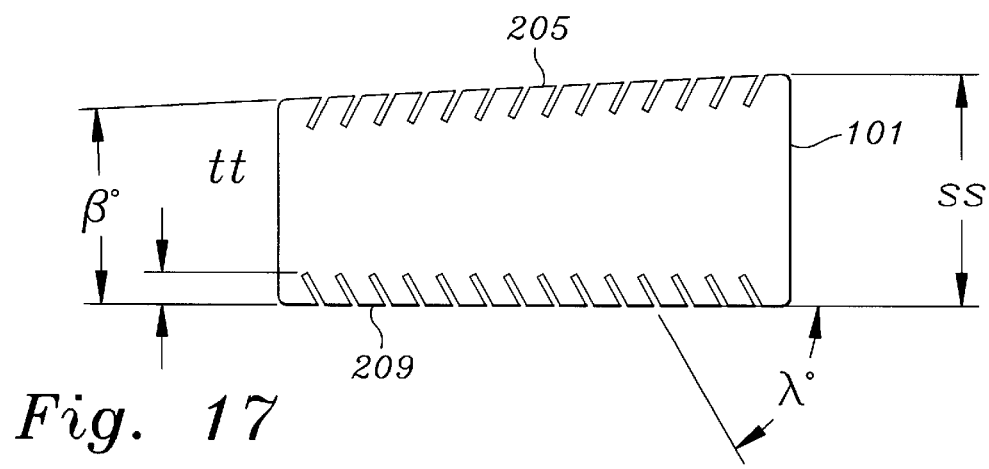
Referring to FIG. 17, a side view of the implant 201 is shown, along line 17—17 of FIG. 16.

Referring to FIG. 17, a side view of the implant 201 is shown, along line 17—17 of FIG. 16. The implant 201, and in particular FIG. 17 is shown as having a linear side profile to facilitate discussion of the underlying geometry. As will be seen beginning with FIG. 17, preferred geometry variations will enable an implant such as implant 201 to fit within the more ellipsoid intervertebral disc space. The side profile of the implant 201 is frusto-conically wedge shaped. A maximum dimension of the height of the implant 201 is shown as a dimension "ss" which may be from about ten to about twenty millimeters high. The angle of the wedge shape is shown by angle β and has an angular magnitude of from about three to about five degrees. The implant 201 is typically implaced with the relatively narrower side of the implant 201 directed into the inter vertebral space, and thus it may have a natural tendency to be urged out of its resting place.

The series of line slots 207 are seen on the upper surface 205 and a lower surface 209. The line slots 207 have a width and angularity with respect to top and bottom surfaces 205 and 209. The spacing between the line slots 207 is preferably about three millimeters, however such spacing may vary, line slots 207 may be unevenly spaced, and the angularity of each line slot 207 may vary, even on the same implant 201. The line slots 207 may have an angle with respect to the top and bottom surfaces 205 and 209 of λ° which has an angular magnitude from about fifty degrees to about seventy degrees. By the law of sines and cosines, the actual depth of each slot will depend upon its angularity at a given depth of extent into the surfaces 205 and 209. The depth, into the surfaces 205 and 209 into which the line slots 207 are cut is shown as a dimension "tt" which may be from about one to about one and a half millimeters. The width of the line slots 207 are preferably from about eight-tenths of a millimeter to one millimeters. The spacing of the cuts or slot are preferably from about three to five millimeters apart and more preferably about four millimeters apart.

The use of line slots 207 have several advantages. First, the formation of line slots provide more surface area to promote bone growth and a stronger fusion with the adjacent vertebra. Second, the angularity of the line slots 207 create a barb effect which makes it far less likely that the implant 201 will reversibly dislodge from its position between adjacent vertebra. The need for a buttress locking plate and the dangers of introducing unwanted and dangerous metal into the human body is thus eliminated. The line slots 207 can also be used in conjunction with a grasping tool upon insertion. All of the preparations described for femoral ring bone implant 201, as a harvested human bone implant, can also be applied to non bone material such as a coral based hydroxyapatite, or to other human harvest materials such as humerus rings and the like and or xenograft materials.

Figure 18:
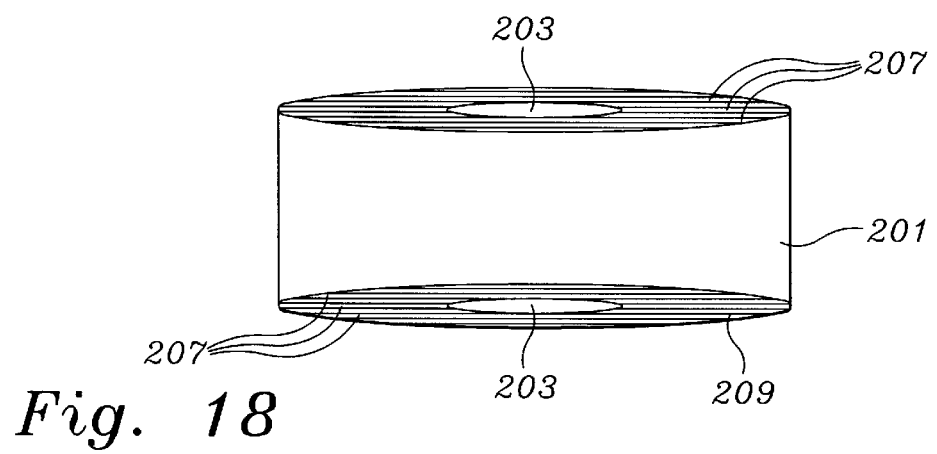
Referring to FIG. 18, a front view along line 18—18 of FIG. 16 is a front view of the implant of FIG. 16 and seen having corners of somewhat softened roundness.

Referring to FIG. 18, a front view along line 18—18 of FIG. 16 is a front view of the implant 201 and seen having corners of somewhat softened roundness. The anterior edge of the implant 201 is seen. The relatively straight lateral profile of the implant is seen in FIGS. 16–18 to illustrate the overall wedge shape in as understandable manner as possible. The use of a flattened upper and lower surfaces 205 and 207 is possible, but one or both of the upper and lower surfaces 205 and 207 may be curved along two axes from the center in order to better fit within the ellipsoidal space between adjacent vertebra.

Referring to FIG. 19, an implant 210 is in side perspective as having a first curved surface 211 and which also includes the line slots 207. A second surface 209 is the same as was seen for implant 201 seen in FIG. 17, since implant 210 has only one of its surfaces modified. Again the depth and orientation of the line slots 207 are so as to promote insertion, with a posterior end 212 having more rounded upper and lower edges (seen as corners in FIG. 18), and with an anterior end 213 having relatively sharp upper and lower edges (seen as corners in FIG. 18), in order to provide anterior support which is of more need in supporting the above located and below located vertebra of the spine once the implant 210 is implanted.

Referring to FIG. 20, a view of the implant 210 looking into the posterior end of the implant 210, in a position similar to that seen in FIG. 18, illustrates the planar lower surface 209 seen in relation to the first curved surface 211, with the line slots 207 extending from left to right across the front half and a bit more of the first curved surface 211 which is visible in FIG. 20.

Referring to FIG. 21 a side view of an implant 214 having the same first curved surface 211 and in addition, a second curved surface 215 is seen. Again, the posterior end 212 and anterior end 213 are seen. The first and second curved surfaces 211 and 215 are seen to match the intervertebral space to enable the implant 214 to fit snugly, evenly and in a trapped fashion within the intervertebral space. Again, the depth and orientation of the line slots 207 are so as to promote insertion, with a posterior end 212 having more rounded upper and lower edges (seen as corners in FIG. 19), and with an anterior end 213 having relatively sharp upper and lower edges (seen as corners in FIG. 19), in order to provide anterior support which is of more need in supporting the above located and below located vertebra of the spine once the implant 210 is implanted, even where the first and second curved surfaces 211 and 215 are present.

Referring to FIG. 22, a further variation, hypothetically beginning with the design of FIG. 20 is seen. An implant 216 is seen from generally the same perspective as implant 201 was seen in FIG. 16. Posterior end 212 and anterior end 213 are seen to orient the viewer on the direction of movement for implacement of the implant 216. A set of linear line slots 207 extends along a central corridor on the first curved surface 211 of the implant 216. These line slots 207 are preferably inclined in the same manner as was seen in FIG. 21. Linear in this sense means that the line slots 207 extend straight with respect to a look down of the first curved surface 211. To the left and the right of the central corridor of line slots 207 are a series of line slots 217 which are oriented at an angle to the linear extent of the line slots 207. The angle is shown by an extension to the lower right of a line taken from one of the line slots 207 and which meets an extension line from one of the line slots 217. The angle shown as angle "ω" (omega) which is preferably from about fifty degrees to about seventy degrees, and more preferably about thirty degrees, but may vary significantly from this angle. Since both the line slots 207 and 217 are angled, it may be preferably to cut line slots 207 and 217 with a laser or micro drill. The transition between the outer extent of the central corridor of line slots 207 and the flanking line slots 217 may or may not involve a sweep at the base of the line slots 207 and 217 at the transition, and the line slots 207 and 217 may or may not be continuous at or communicate with respect to the depth of the base of their slot structures.

The line slots 207 will enable grasping by a structure having linear raised portions which mate with the line slots 207, while the line slots 217 more readily indicate the direction of entry for insertion of the implant into the inter vertebral space. The upper appearance of the line slots 217 with respect to the line slots 207 create an arrow impression and indicate the direction of insert which both enables a surgical assistant to register the implant 216 into an impact holder, and also enables the surgeon to in an instant check the orientation of the implant 216 for insertion and with regard to its registration in an impact holder.

Figure 23:
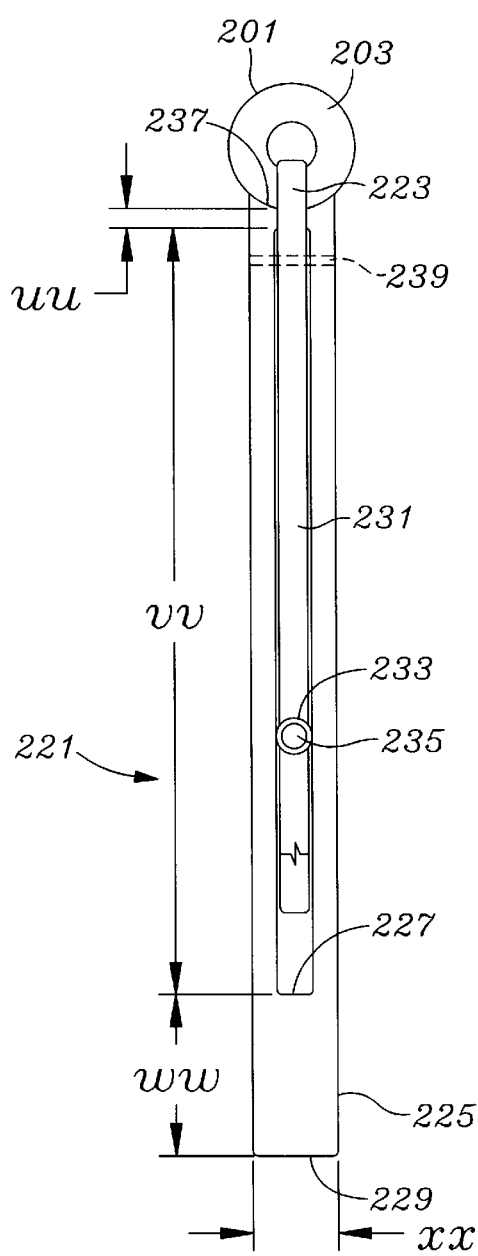
Referring to FIG. 23, a top view of a combination implant holder and impact tool is shown with a bone implant being grasped.

Referring to FIG. 23, a top view of a combination implant 201 holder and impact tool is seen as an implant holder-impactor 221. An implant 201 is seen as being grasped by one grasping jaw 223 of a pliers-like combination which operate within an impact frame 225. Impact frame 225 has a central through opening 227 to accommodate lever jaw combinations of which the lever portion 231 of one lever jaw member is predominantly seen in FIG. 23 and the grasping jaw 223 of the other lever jaw combination is seen. A portion of the rear of lever portion 231 is broken away in order to show the central through opening 227. A butt-end 229 of the impact frame 225 is significantly away from the rear terminus of the through opening 227. Extending the lever portion 231 beyond the through opening 227 enables the rear of the impact frame 225 to stabilize the lever portions including lever portion 231 so that they do not pass through the through opening 227. A thumb adjust nut 233 engages an aperture in the lever portion 231 and against another lever portion to hold the implant 210 in place. The impact frame 225 has a curved end surface 237 designed to apply even impact force to an implant 201 about its generally circular periphery. The implant 201 is grasped over less than half of its diameter. There is preferably some longitudinal clearance space between the impact frame 225 and the lever jaw members as they grasp the implant 201. This enables the impact force to be transmitted directly to the implant 201 about its generally cylindrical periphery to thus spread the impact force efficiently, and to prevent significant impact from being transmitted onto the surfaces of the implant 201 which are grasped by the jaws of the lever jaw members. A pivot structure which may be referred to as a cross pin member 239 may be of several types and may enable the lever jaw members to pivot with respect to each other, and preferably to be adjustable in terms of the size of the implant 201 they engage, as well as to shift linearly with respect to the impact frame 225. As such, the cross pin member 239 as seen only to indicate some structure which defines pivot, and need not even be a pin. Cross pin member 239 may indicate a more integrated structure to permit pivoting.

Figure 24:
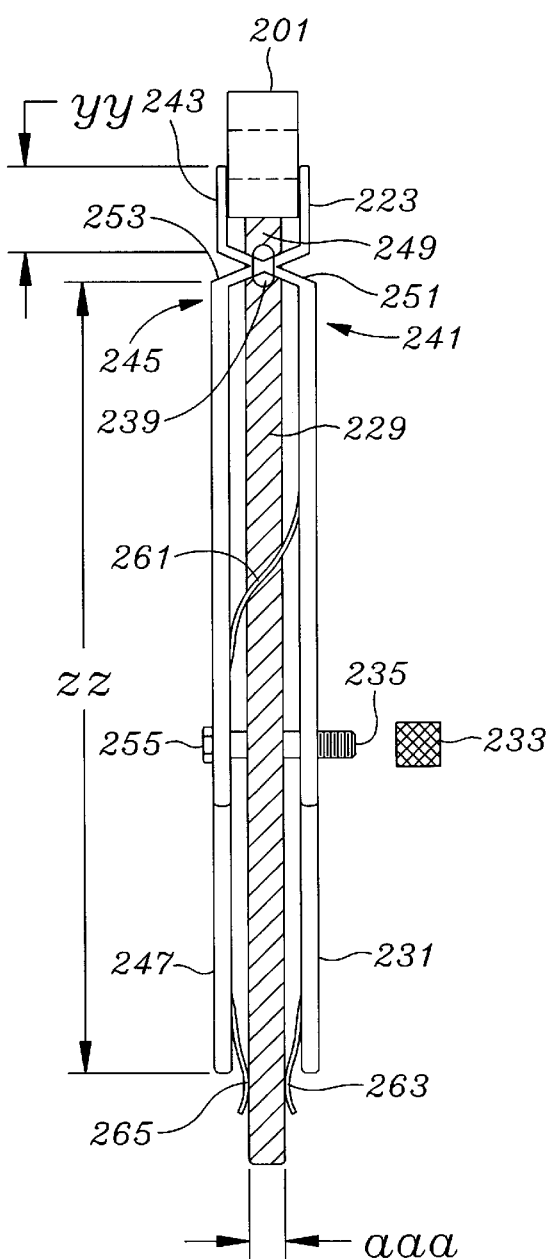
Referring to FIG. 24, a side view of the impactor of FIG. 23 illustrates jaw members and knife springs.

Referring to FIG. 24, a side view of the impactor 221 is seen and further details are illustrated. Lever portion 231 is a part of a lever jaw combination 241 and includes a jaw member 243. Grasping jaw 223 is a part of a lever jaw combination 245 and includes a lever member 247. Lever jaw combinations 241 and 245 have transition portions 251 and 253, respectively A oval shaped pin aperture 249 is provided to enable the lever jaw combinations 245 to move forwardly and rearwardly with respect to the impact frame 225. The existence of the oval shaped pin aperture 249 and the central through opening 227 insure that the impactor 221 smallest aspects will be openly subject to sterilization techniques. Also seen is a bolt head 255 of the bolt 235 which extends through lever members 247 and 231. Aside from issues of adjustability, the impactor 221 will be used by resting an implant 201 against curved end surface 237. The levers 231 and 247 are begun to be brought together to cause the grasping jaws 223 and 243 to close on the implant 201. Just before the jaws 223 and 243 engage the implant, the lever jaw combinations 241 and 245 are moved so that their cross pin member 239 or other pivoting structure is most nearly in the center of the oval shaped pin aperture 249 so that the impact frame 225 will solely be responsible for imparting impact energy to the implant 201. The levers 231 and 247 are then brought completely together to cause the grasping jaws 223 and 243 to close on the implant 201 while the cross pin member 239 or other pivoting structure is most nearly in the center of the oval shaped pin aperture 249. The thumb nut adjustment is tightened down on the lever portion 239 to provide an independent holding force on the implant 201 to further free the surgeon's hands and attention to impactive implacement without having to worry about holding pressures and the like. In addition, this device is such that other medical personnel can assemble the implant 201 into the impactor 221 to further enable pre-preparation by others and to save valuable time during the operative procedure.

Also seen in FIG. 24 is a blade spring 261 attached to lever member 247 and which extends from the lever member 247, through the central through opening 227 and against the lever member 231. Blade spring 261 urges the lever members 231 and 247 apart from each other so that a user can position the implant 201 and perform an adjustment of the lever jaw combinations 241 & 245 with one hand steadying the implant and the other adjusting the thumb adjustment nut 233 while the user watches the cross pin member 239 within the oval shaped pin aperture 249. Thus the makeup of the impactor 221 and the implant 201 can be done by a single surgical professional with two hands, quickly and easily.

The dimensions of the impactor 221 may vary widely but preferred dimensions will be set forth. Referring to FIG. 23, a distance of magnitude "uu" exists between the outside terminus of the lever member 247 and the beginning of the central through opening 227 and is preferably about one centimeter. The length of the central through opening 227 has a magnitude "vv" which is preferably about twenty four centimeters. The length of the impact frame 225 between the end of the central through opening 227 and the butt-end 229 has a magnitude "ww" of about fifteen centimeters. The width of the butt-end 229 has a magnitude "xx" of about thirty centimeters. At FIG. 24, the length of the jaw members 243 and 223 has a magnitude "yy" of about twenty five millimeters. The length of the lever members 231 & 247 has a magnitude "zz" of about twenty five centimeters. The thickness of the impact frame 225 is seen to have a magnitude "aaa" of about twenty five millimeters. The crossing of the "X" pattern between the jaw members 243 and 223 and the lever members 231 & 247 may be from about two millimeters to about twenty millimeters, and will depend upon the thickness of the impact frame 225 dimension "aaa", and other considerations.

Another alternative would be the use of a blade spring 263 attached to the lever portion 231 and extending to make contact with the impact frame 225 in a position between the rearmost extent of central through opening 227 and butt end 229. Likewise, lever portion 247 can have a blade spring 265. The overhang of the lever portions 231 and 247 rearwardly beyond the extent of the through opening 227 provides the bulk of the stability, with knife springs 263 and 265 being relatively weak and tending to reduce clanking and to keep the lever portions 231 and 247 generally linear with respect to the impact frame 225.

Figure 25:
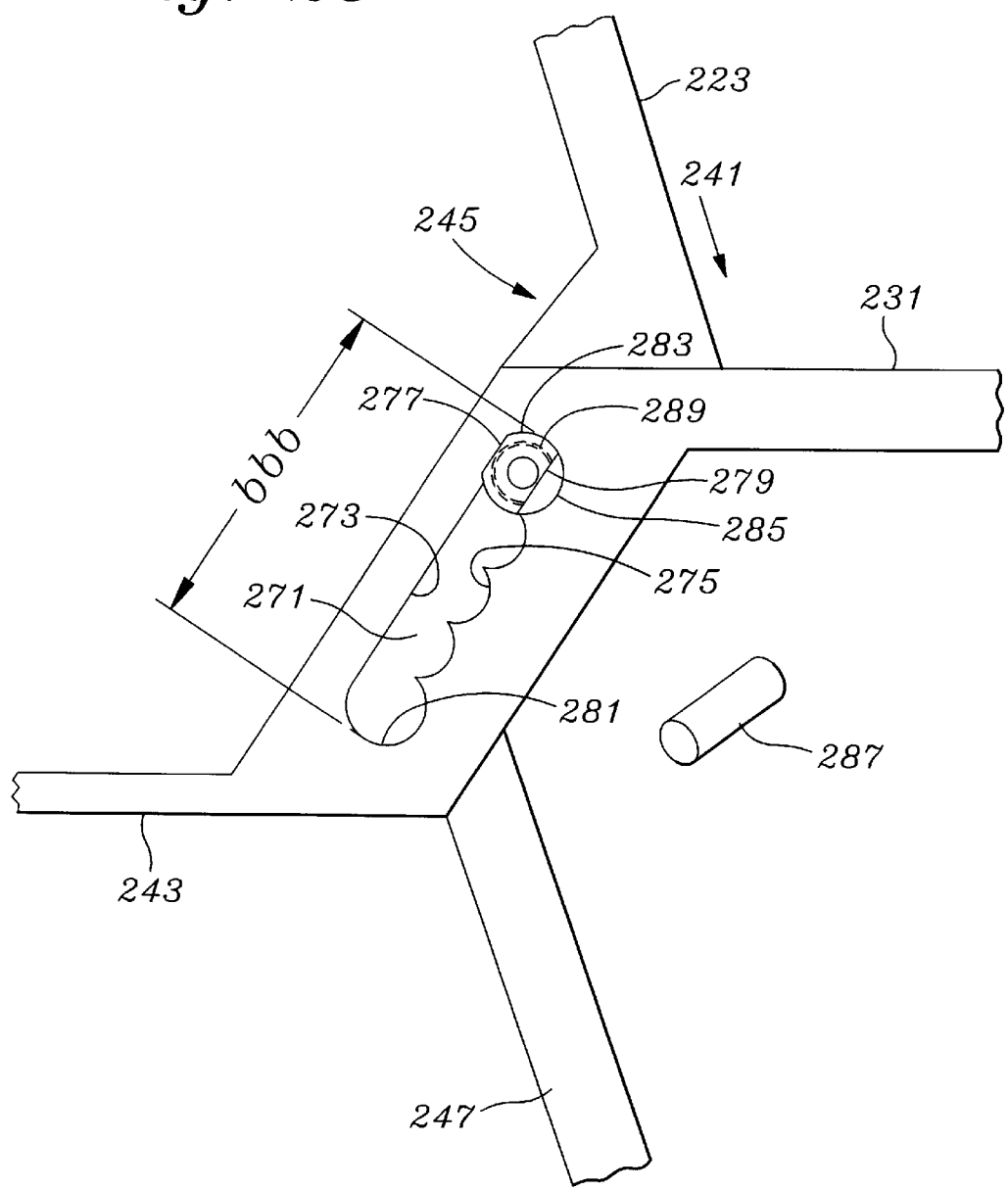
Referring to FIG. 25, an example of the workability of the lever jaw combinations seen in FIGS. 23 and 24 are shown.

Given that the lever jaw combinations 241 & 245 will not be used other than to position the implant 201 in front of the curved end surface 237, these members can be relatively slender. One example of the workability of the lever jaw combinations 241 & 245 of the invention is seen in FIG. 25. The lever jaw combinations 241 & 245 of the invention have been opened with respect to each other and removed from the impact frame 225. The cross pin member 239 is removed as a pre-requisite to removal of the lever jaw combinations 241 & 245 from the frame 225, as will be shown. The lever jaw combination 245 is pictured behind the lever jaw combination 241. In the descriptions which follow the structures which are associated with either of the lever jaw combinations 241 & 245 could be associated with the other.

Lever jaw combination 241 in the foreground includes an adjustment slot 271 which may have a straight side 273 and an undulating side 275 consisting of arc sections having a radius of about the width of the adjustment slot 271. Five such arc sections are shown, with the last two arc sections continuing in a more circular fashion forming the termination of the adjustment slot 271.

Lever jaw combination 245 includes an annular post 277 (seen in dashed line format) seen just inside the extent of the boundary of the adjustment slot 271, and having a generally circular extent but interrupted by a chord section removed to form a chord shaped flat 279 which is just narrow enough to enable the annular post 277 to move along the adjustment slot 271 barely clearing by each minimum width point of the adjustment slot 271 between each of the circular undulations of the undulating side 275. The lower end of the slot has a relatively larger radius opening 281 to enable a relatively larger cap 283 sitting atop annular post 277 to slip through the relatively larger radius opening 281 to enable the removal of the lever jaw combination 241 from the lever jaw combinations 245 for a complete break down of the impactor 221. Complete break down insures complete sterilization.

On assembly, larger cap 283 is inserted through the larger radius opening 281, while the lever members 231 & 247 are kept wide apart as shown in FIG. 25, the annular post 277 may be moved along the slot 271 to any one of the four upper positions shown. In the alternative, larger radius opening 281 may be eliminated while an opposing chord 285 may be provided to enable the larger cap 283 to escape from the slot 271.

In any event, once the lever members 231 & 247 are assembled, they are positioned within the central through opening 227. A pin 287 may be placed through an aperture 289 extending through the middle of the annular post 277. The pin 287 may be a pressure fit pin which can be inserted manually and need only have enough force characteristic to loosely hold the lever members 231 & 247 within the central through opening 227.

Although a relatively large oval shaped pin aperture 249 is shown, and which will give a lot of play to any pin 287, the size can be adjusted to give a much closer fit. In addition, the material surrounding the oval shaped pin aperture 249 can be used to help set the pin 287. Pin 287 can be a rolled annular tube or other stress relieving device. Pin 287 can be permanent, for example, where the central through opening 227 contains a slot with rear entry and enabling the pin to enter and slide to the front of the impact frame 225. In this case, structures including the pin 287, annular post 277, chord shaped flat 279, and larger cap 283 may be made permanently attached to one of the lever jaw combinations 241 & 245 to avoid the use of smaller removable parts. As can be seen, the preferable length of the adjustment slot 271 is a magnitude along a length "bbb" preferably about one centimeter.

Referring to FIG. 26, the lever jaw combination 241 is shown in much the same orientation it was seen in FIG. 23, but with removal of the underlying lever jaw combination 245 and impact frame 225. The lever portion has a transition portion 251 which may include some structure relating to the cross pin member representation seen in FIG. 23. Seen for the first time is a face 291 of the jaw member 243. The face 291 may have structure for secure grasping. In FIG. 26, as series of raised furrows or raised line members 293. The raised line members 293 may have a height and spacing which matches and is complementary to the possibly evenly spaced line slots 207 of the implant 201 or implant 216. In this case, it would help the surgical professional preparing the implant 201 into the impactor 221 to orient the implants 201 or 216 properly. In some cases, the raised line members may be slanted to match a slant of the possibly evenly spaced line slots 207 where such can be done without damaging the material immediately around the possibly evenly spaced line slots 207.

In another possible embodiment, the line slots 207 may be unevenly spaced in accord with a pre-arranged pattern matching a pattern of raised line members 293 of the lever jaw combination 241. This may help or force a surgical worker preparing the implant 201 into the impactor to position it properly. Referring to FIG. 27, an implant 295 is pictured having a first array of line slots over a portion 297 over which the line slots 207 are relatively wider spaced, perhaps to match the raised line members 293 of FIG. 27. A second array of line slots are much more closely spaced over a portion 299 of the implant 295. The opposite side of implant 295 would be a mirror image of the view of FIG. 27. In addition, where implant 201 has a frusto-conical profile, the jaw member 243 could also be appropriately angled, or jaw member 243 may be slalom shaped to insure an even grip over a significant area of the implant 201 or 295 even where the angle of grasp changes, either due to a size shift in the implant 201 or 295, or to an adjustment of the lever jaw combinations 241 and 245 not achieving an optimum angular grasp of the implant 201 or 295. This may be the case where the optimum relationship may exist between the existing detent dimensions or size selections between the sizes available with respect to the lever jaw combinations 241 and 245. In addition, the implant 201 may be marked to aid workers in orienting it.

Referring to FIG. 28, a completion impactor 301 includes an extension fore end section 303 which fits into handle portion 105 seen in FIG. 8. All of the details of handle portion 105 will not be further discussed. Extension fore end section 303 includes a stepped inward insertion member similar to stepped inward insertion member 125 seen in FIG. 8, and is seen having burled portion 305 at the base of an extension 307. Extension 307 has an end portion 309 which includes a widened area having an inwardly curved end 311 having a radius or curvature compatible with urging a twenty five to thirty millimeter diameter cylindrically side walled shape implant 201 or 295. A scale 313 is seen spaced along a path from the curved end 311 and toward the handle portion 105.

The impactor 301 is a final setting or completion impactor used to finish seating the implant 201 or 295 once it has been initially introduced by the impactor 101. Impactor 101 is used to introduce the implant 201 or 295 into the intervertebral space preferably not beyond the extent of the ends of the grasping jaws 223 and 243. This extent can clearly be seen by the surgeon, and avoiding extending the grasping jaws 223 and 243 is thus easily avoided. Once the impactor 101 is removed from the implant 201 or 295, the impactor 301 is used both to complete placement into the intervertebral disc space with the scale 313 and the centering indication of the extension 307 serving as the surgeon's guide. As is seen in FIG. 28, the linear width of the arc of curved end 311 has a magnitude indicated by "ccc" of about two centimeters.

Referring to FIG. 29, an end view of the curved end 311 of the impactor 301 is seen. The thickness of the impactor curved end 311 has a magnitude indicated by "ddd" of about eight millimeters. Note in FIG. 28 the rounded corners to maximize the safety of impactor 301.

The procedure for best utilization of the instruments disclosed in a typical fusion operative procedure include standard surgical techniques for first exposing the anterior lumbar spine trans peritoneal or retro peritoneal. The greater vessels in the operative area are then retracted off of the spine working level. Consideration of the greater vessels and safety in working around them are a significant consideration of this patent application.

Figure 30:
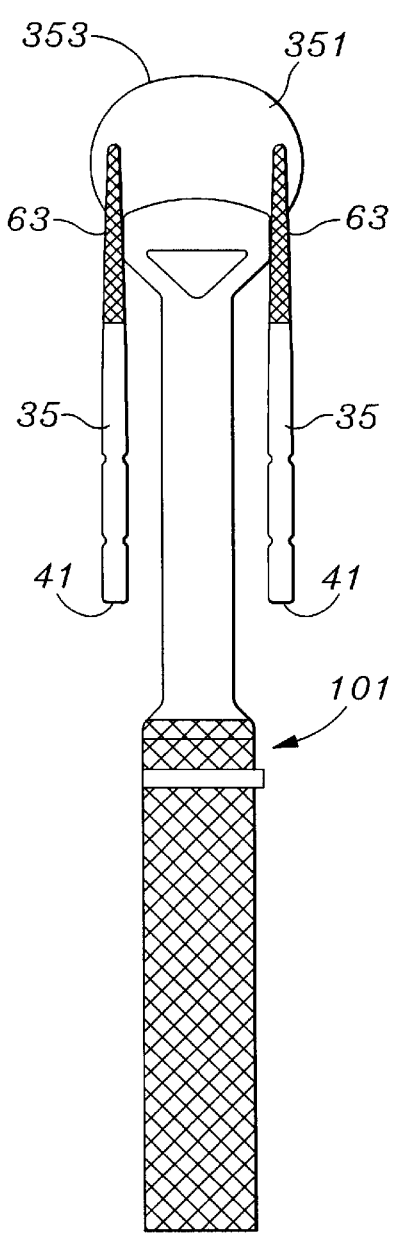
Referring to FIG. 30 a top view looking down on a lower vertebra from a point of view of a vertebra which would normally be located over it illustrates has two distractor tip portions and a box chisel entering the disc space therebetween.

Next, a disectomy is performed with scalpel, curettes and rongeurs. The anterior lip of the adjacent end plates is slightly removed. Next, the disc space and cartilage between two adjacent vertebra which is to be replaced is distracted with a pair of distractor 31 described in this application. The insertion of the distractors 31 into the disc space may be accomplished by insertion of the tip portion into the disc space as is seen in FIG. 30. The view of FIG. 30 is a top view looking down on a lower vertebra 351 from a point of view of a vertebra located over it, which has two tip portions 35 extending into the disc space on either side and which is seen with a box chisel 101 entering the disc space between the tip portions 35. The vertebra 351 has a posterior end or border labeled clearly by the numeral 353, with the two tip portions 35 and box chisel 101 entering from the opposite anterior side.

To further illustrate the orientation of the tip portions 35, the lower end 41 is showing dimension "l", and the locking slots 43 and 45 can be seen. The tip portions can achieve the position seen in FIG. 30 in one of several ways. Where the burled, or rasp surface 63 is present on the tip portions 35, insertion into the intervertebral space in the orientation shown in FIG. 30 performs a "filing" or "rasping" action on the vertebra to form a small notch above and below which tends to stabilize the tip portion 35 from rotation about its axis. The tip portion 35 is inserted while the handle portion 33 is attached and with the handle portion 33, the surgeon has a good deal of manual leverage in inserting the tip portion 35. The tip portion can be inserted probingly back and forth to help form the stabilization notch. The distractor 31 will be inserted so that the tip portion is most nearly vertical with respect to the tip portion 35. The distractor 31 can be inserted with manual force, or preferably impact force since impact force is easier to control the depth inserted. The scale 42 on both of the tip portions 35 and 65 also assist in controlling the depth. After both of the distractor 31 tip portions of the same size, of which either 35 or 65 are but two examples, are inserted to the proper depth, the handle portion 33 may be removed from its respective tip portions 35 or 65. This frees the surgical field from the physical presence of the bulk of the handle portions 33 which were so advantageous in positioning the tip portions 35 or 65.

The distractors 31 should have tip portions, such as tip portions 35 and 65 selected to provide sufficient inter vertebral disc space or spread only to the extent necessary to insert the implants 201, 210, 216 or 295. A spacing of at least about sixteen millimeters will be sufficient to admit the box chisel 101. The box chisel 101 is inserted preferably with impact force and utilizing the scale 116 to monitor the depth of insertive cut. The impact surface 139 can be used to back the chisel insert portion 103 and the whole box chisel 101 out of the intervertebral space 355. The material which collects in the inside of the box cutting portion 109 can be removed either by tapping the end or by insertion of a flexible body into the through opening 111 and directed into the inside of the box cutting portion 109 in the direction of the curved end 107. The procedure may be re-applied and the box chisel 101 used to provide a disc space which extends into the intervertebral space about five millimeters short of the posterior border of the end plates of the adjacent vertebra, which is about five millimeters from the posterior end border 353 seen in FIG. 31. This degree of clearance will enable and allow insertion of the implant such as femoral ring implant 201, having a diameter of from about twenty five to about thirty five millimeters.

Once the box chisel is inserted and re-inserted to the extent that, in the judgement of the surgeon, enough material is removed, the box chisel 101 is removed from the intervertebral space. The curette 161 is then used to complete any removal of material to insure that fusion can take place more rapidly and to clear much of a space for proper fitting of the implants 201, 210, 216 or 295 as is possible. The goal is to eliminate any material which might interfere with the implants 201, 210, 216 or 295, but while removing as little adjacent living bone material as possible which would otherwise participate in the fusive growth.

Next, one of the implants 201, 210, 216 or 295 is secured within an impactor, such as impactor 221. Any one of the implants 201, 210, 216 or 295 used is properly registered within the impactor 221, the thumb adjust nut 233 tightened to cause the grasping jaws 223 243 to close and engage on the implant 201, 210, 216 or 295 selected. The impactor is positioned to cause the posterior side of the implant 201, 210, 216 or 295 to be positioned to enter into the intervertebral space anterior opening. The surgeon then uses an impact device, such as a hammer or heavy rod, to strike butt-end 229 of the impactor 221, to cause the approximately two-thirds portion of the implants 201, 210, 216 or 295 which lie ahead of the portion engaged by the grasping jaws 223 and 243 to enter the intervertebral space. Where the implants 216 is utilized, the middle portion will represent the maximum amount of displacement between the adjacent vertebra which needs to be cleared. Assuming that the surgeon has inserted just over half or just over five eighths of the diameter of the implant 201, 210, 216 or 295 into the intervertebral space, the thumb adjust nut 233 may be loosened to cause the grasping jaws 223 243 to loosen and disengage the implant 201, 210, 216 or 295 selected. The completion impactor 301 may now be employed against the anterior surface of the thumb adjust nut 233 tightened to cause the grasping jaws 223 243 to close and engage on the implant 201, 210, 216 or 295 and impacted to continue the progression of travel into the intervertebral area until its rest position is achieved. The scale 313 on the completion impactor can be used to precisely position the implant 201, 210, 216 or 295 into the intervertebral space, perhaps accompanied with a scale probe inserted into the intervertebral space to gauge its exact posterior to anterior extent.

Figure 31:
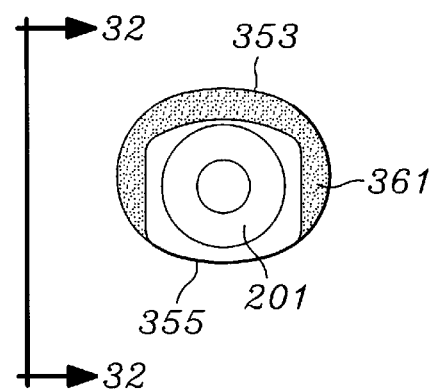
FIG. 31 is a view taken looking down into a mid sectional view of a vertebra illustrating location of an implant.

Once the implant 201, 210, 216 or 295 is placed in its resting position, its surroundings should be substantially as is shown in FIG. 31. An anterior side 355 of the vertebra 351 is now seen. The stippled area surrounding the implant 201, shown for example, and representing implant 201, 210, 216 or 295, is the material which may remain and which is not needed to be removed completely both for safety and to minimize disruption to the surrounding areas.

Figure 32:
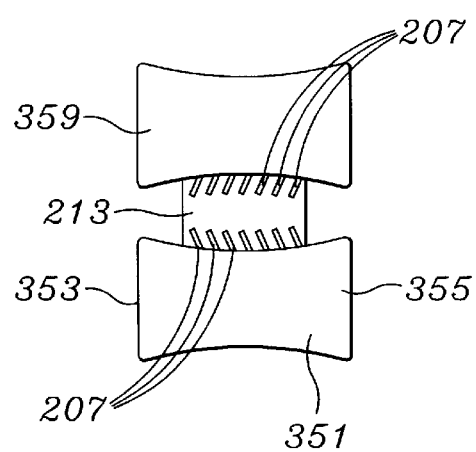
Referring to FIG. 32, a view looking into the spine along line 32—32 of FIG. 31, and with an implant shown in position.

Referring to FIG. 32, a view looking into the spine along line 32—32 of FIG. 31, and with the implant 214, for example, shows the position of the implant 214 which was inserted across the anterior end 355 of vertebra 351. Note the orientation and depth of the line slots 207 and how they are swept toward the intervertebral entry space. Also seen are a pair of lines 361 and 363 which indicate the angle of lordosis. The bone graft implant 214 is shown as being locked in the recesses of the upper and lower vertebras 351 and 359 due to the biconvex shape of the implant 214 and the concave lower surface of vertebra 359 and the concave upper surface of vertebra 351.

Figure 33:
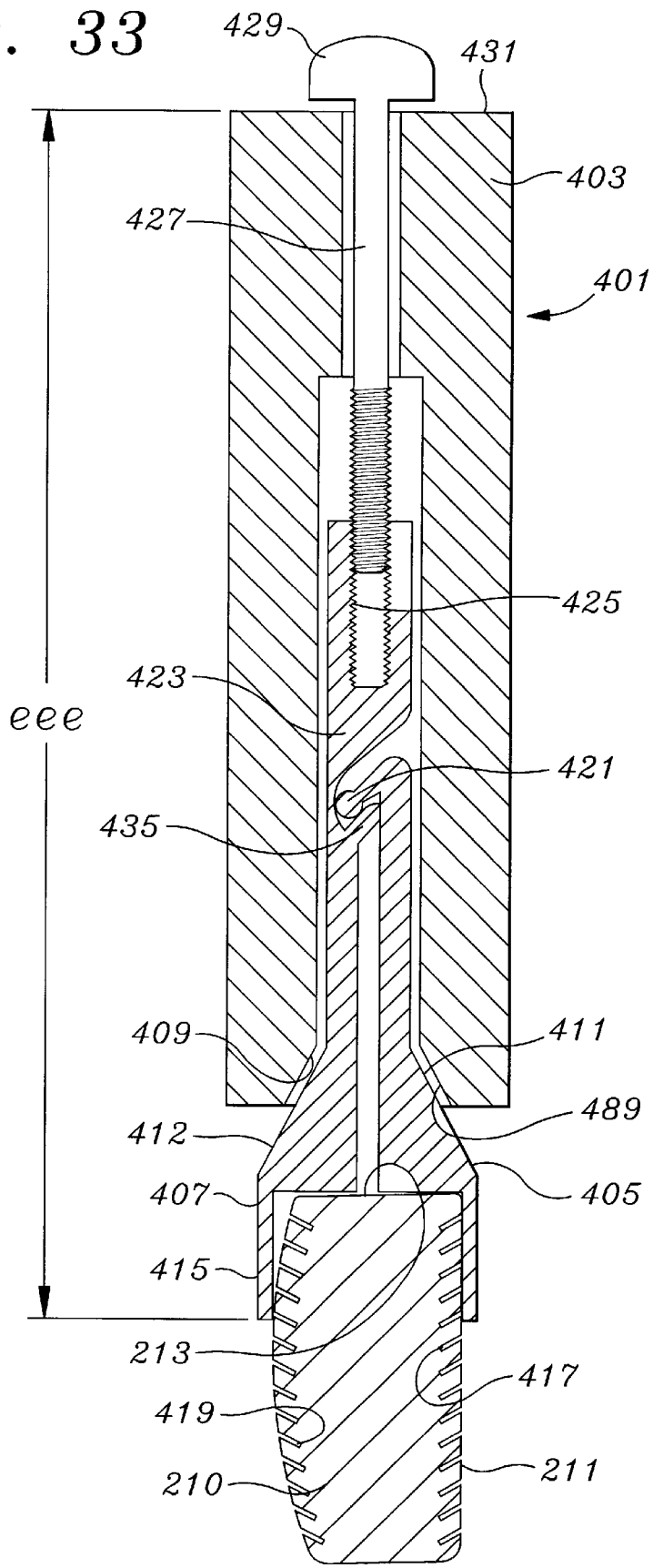
Referring to FIG. 33, a side sectional view of an alternative impactor is illustrated.

Referring to FIG. 33, a side sectional view of an alternative impactor 401 is illustrated. Impactor 401 includes an outer sleeve 403 to act as a housing to cause closure of a first jaw 405 which pivots with respect to a second jaw 407 when the drawn inside the outer sleeve 403. An angled entrance 409 may be advantageously formed and positioned with respect to a back surface 411 to control the withdrawal force to clamping force characteristic. Second jaw 407 has a back surface 412 to also engage an angled entrance 409 most closely adjacent to it. For illustration purposes, implant 210 is used to show the possible shapes for the grasping portions 415 and 417 of the jaws 407 and 405. The surface 209 of the implant 210 is relatively straight, but at an angle with respect to the anterior side 213. The grasping portion 417 is thus also similarly angled. The first curved surface 211 if the implant 210 is curved and an inside of grasping portion may have a surface 419 to either be curved to complement the surface 211 where the inside surface of the grasping portion 417 is such that distributed surface friction is the main holding mechanism, or it may be curve to concentrate the surface friction engagement, perhaps with some resulting point contact deformation of the implant 210.

The arrangement shown has the first pivoting jaw 405 having a pivot member 421 with respect to a main body 423 of the second pivoting jaw 407. The main body 423 includes a threaded bore 425 which is engaged by an elongate draw bolt 427 having an impact head 429. The impact head 429 will always tightly rest against a butt-end 431 of the impactor 401 when the jaws 405 and 407 are withdrawn into the outer sleeve 403. The pivot member 421 will typically include a pin type or rotationally smooth structure which interacts with a slot 435 seen has having a reverse angular extension and for pivot member 421, and angled to an extent more than necessary to adequately apply a pulling force to the pivot member 21. The arrangement between pivot member 421 and slot 435 need not be angled at all, the only relationship necessary is that one member engaged the other as it is drawn into the sleeve 403. With this type of configuration, if the draw bolt 427 is completely disengaged from the threaded bore 425, the jaws 405 and 407 will slide through the outer sleeve 403 and fall away from each other and the impactor 431 will then produce only four parts with all surfaces exposed for sterilization. Lengths and ratios of lengths of the individual components may vary, but the overall length is shown by a dimension "ccc" Other variations of the impactor 401 are possible.

Figure 34:
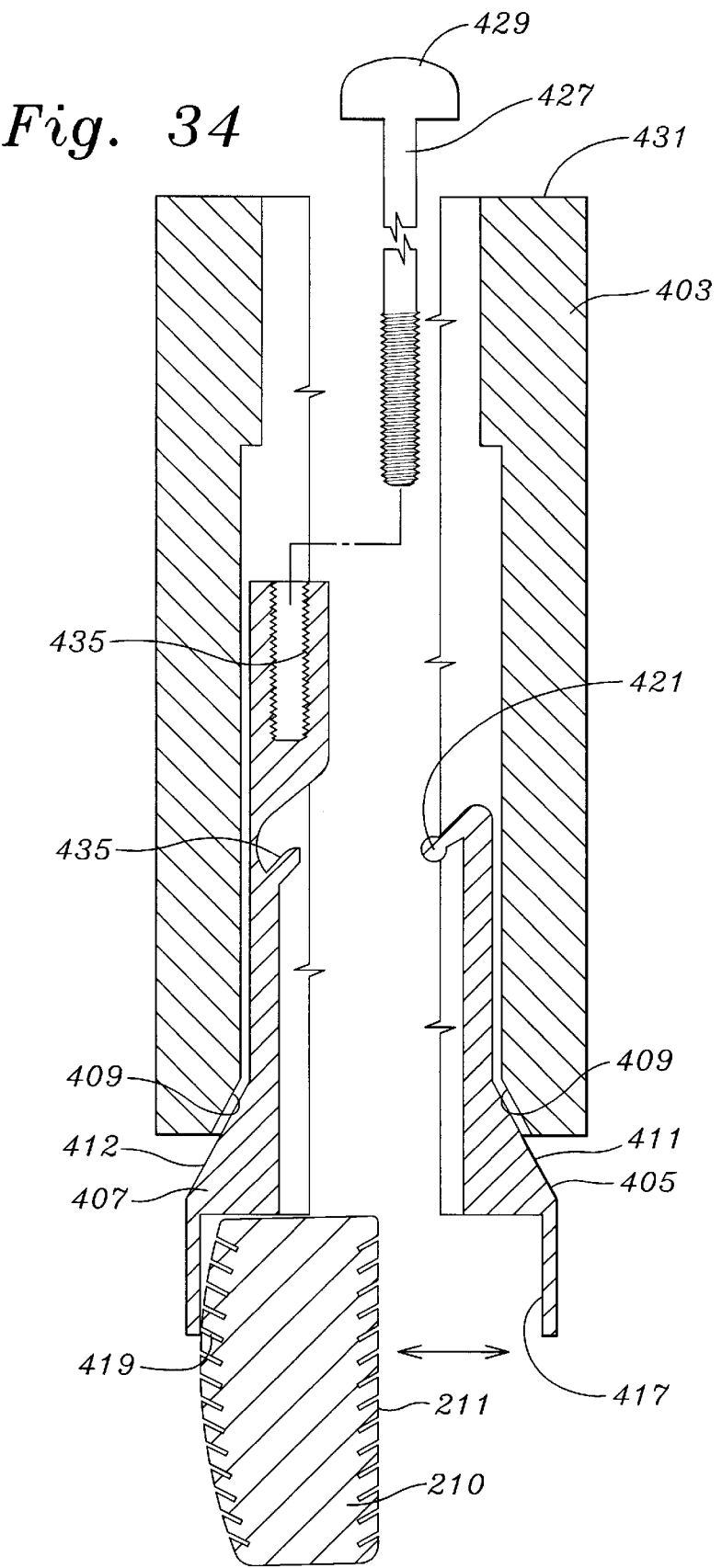
FIG. 34 is an exploded view of the structure seen in FIG. 33.

FIG. 34 shows an exploded view of FIG. 33, and illustrates the manner of connection and disconnection of the slot 435 with respect to the pivot member 421. As can be seen, once the draw bolt 427 is disengaged from the main body 423, the main body 423 along with the first pivoting jaw 405 can exit the end of the sleeve 403 and become completely disassembled for sterilization in only four parts.

Additional instruments provide additional tools for the surgeon to assist the surgeon in both the anterior and anterolateral procedures to perform the procedure much more quickly and exactly. These instruments produce more uniformity in result in a quicker time, and also will result in a significant reduction in waste in expensive medical implant structures.

Referring to FIG. 35, an anterior type intervertebral cylindrically directed or peripheral rasp 451 is seen, having an anatomical shape. By cylindrical it is meant that the main perimeter is outwardly directed in a generally The use of the rasp 451 will typically occur after the discectomy is completed, with the rasp 451 being inserted into the intervertebral disc space to remove and shape an amount of remaining fibrocartilagenous material and to quickly shape the space precisely to accommodate an anatomically shaped implant to be shown later. The rasp 451 enables the surgeon to concentrate on forming the periphery of the intervertebral disc space especially posterior where access and any other type of instrument is difficult and potentially dangerous. The use of the rasp 451 may be also valuable after using a roughing rasp, seen below, which may be used to make the first rasping removal of a combination of material both from the bone plate and the peripheral of the intervertebral space.

The handle portion 105, including its bore 127, open slot 129, locking ring 131, groove 133, burled surface 135, butt end 137 and the dimensions of the handle portion 105 are as was shown in FIG. 8. A rasp insert portion 453 includes a head portion 455 which has a circular shape as seen from the perspective of FIG. 35. A smooth surface 457 faces the observer of FIG. 35, but a rasp surface 458 as is seen with bracketed numbering. Rasp surface 458 is seen as located at least part of the periphery of the head portion 455 with a practical interruption at a shaft 459 and an optional interruption at a side of the head portion 455 opposite the shaft 459, as will be later discussed. The rasp surface 458 is directly radially outwardly from the head portion 455. Rasp surface 458 may include crossing grooves which may be arranged in any pattern. Shaft 459, at the point of connection to the circular side of the head portion 455, includes a scale 460 which shows numbering measured from the farthest point of the other side of the head portion 455. The scale 460 enables the surgeon to immediately at each step of the operation to know how deeply a rasp action is being applied to the human spine.

At the end of the shaft 459 is an expanded portion 461 having a burled surface 463 adjacent a radial surface 465. A groove 467 on an insertion member 469 operates in conjunction with the locking ring 131 seen in FIG. 8. Referring to FIG. 36, a view of the end of the handle 36 reveals the oval nature of the handle portion 135.

The dimensions seen for the rasp 451 of FIG. 35 include a diameter dimension "fff" which may preferably be the same in all directions. The actual dimensions for the diameter of the rasp 451 will be seen to be a part of a system and are thus included in a table below. A dimension "ggg" is shown as the length of the shaft 459 and may preferably be from about 10 to about 20 centimeters in length.

Referring to FIG. 37, a side view of the intervertebral rasp 451 of FIG. 35 illustrates the shape orientation for an anterior procedure, where the rasp 451 is brought from a position anterior to the spinal column and moved in the posterior direction into the intervertebral space. As can be seen, in addition to the face surface 457, a face surface 471 is oppositely disposed with respect to the face surface 457.

The face surface 471 may be of a lesser curvature than the face surface 457 where the peripheral rasp 451 is to be even more specifically shaped for a proper and comfortable working orientation within the intervertebral space. In the typical intervertebral space, each vertebral bone has an upper directed surface which is relatively less curved, and a downwardly directed surface which is relatively more curved. In the side view of FIG. 37, and although it may be somewhat exaggerated for viewabilty, the face surface 471 is relatively less curved and would engage a lower spinal bone surface while the face surface 457 would engage a relatively more curved upper spinal bone plate. This subtle difference is illustrated for as an example of the most customized rasp instrument possible. The difference in curvature is a complex function of the shape as the surfaces are not radiused surfaces and perhaps may be described as a ratio of center height to a height taken at half of the radius to give a simple example of how the two sides may differ. For example, the difference in shapes may be also characterized by: (ex, different heights above the band, spherical, offset center height, etc. You should supply this at a minimum!!!!

The two face surfaces 471 and 457 may be exactly alike in an advantageous, but slightly less than optimal realization. The rasp motion for removal of cartilage material will consist of movement of the shaft 459 to the left and right in FIG. 35 or in a direction into and out of the paper of insertion member 469, as seen in FIG. 37. Angular motion will generally be restricted due not only to the presence of viscera at the entrance to the intervertebral space, but also due to the fact that the posterior surface portion 475 has a narrow height and that the anterior surface portion 477 has a wide height and that too much angular displacement would cause improper operation as by binding and mismatch with the naturally occurring intervertebral bone surfaces.

The surface between the face surfaces 457 and 471 is generally cylindrical but places the face surfaces 457 and 471 to be angled slightly apart from each other in accord with the anatomical angular displacement of the intervertebral surfaces. The rasp surfaces 458 are divided into two general portions or sides, including a side 479 facing the viewer of FIG. 37, and a matching side 481 shown with an arrow hooking around and indicating the back side in FIG. 37. Both of the sides 481 and 479 are separated by a small smooth area 482 at the end of the head portion 455 opposite the point of attachment of the shaft 459, at least for the anterior peripheral rasp 451. The small smooth area 482 provides a relief or interruption to the rasp areas 458 so that the progression toward the spinal canal will be mitigated and so that an even removal of material is accomplished. Since the maximum force in the anterior procedure is typically placed along the shaft 459, the small smooth area 482 mitigates the more rapid invasion in the posterior direction and insures that the removal of material proceeds in a more even radially proceeding manner.

The surrounding rasp surfaces 458, and including the smooth area 482 between the face surfaces 457 and 471 has a minimum extent or width between the face surfaces 457 and 471 at the smooth area 482 and specifically at the posterior end portion 475. The shaft 459 attaches to the head portion 455 at a maximum extent between the face surfaces 457 and 471 at an anterior surface portion 477 irrespective of the presence of the shaft 459.

Measured with respect to an individual's spine, and looking from the posterior surface toward the anterior surface, a surface having a medium extent of separation between the face surfaces 457 and 471 at a left side surface portion 479 is seen in FIG. 37. The right side surface portion 481 is again indicated by an arrow leading to the rear of the peripheral rasp 451, as seen in FIG. 37. Since left side surface portion 479 is in transition between the minimum separation posterior surface portion 475 and maximum separation anterior surface portion 477, the left side surface portion 479 at its mid point appears somewhat wedge shaped because it is in transition between minimum separation posterior surface portion 475 and maximum separation anterior surface portion 477. The mid points of the minimum separation posterior surface portion 475 and maximum separation anterior surface portion 477 approach parallel side edge relationship at their points of minima and maxima, respectively.

The thickness between either the maximum outer dimension of the face surface 471 or the concentric center of its diameter may differ very little. As can be seen in FIG. 37 the surfaces 457 and 471 may be even surfaces and may rise evenly from the transition between surfaces 457 or 471 and the surfaces 477, 479, or 475. As such, the surfaces 457 and 471 may appear to be very slightly inclined toward each other. The dimension "hhh" is seen to be a maximum or near maximum width dimension between the two general maxima of each of the face surfaces 457 and 471. It is this dimension "hhh" which the surgeon may select in a set of rasps 451 to either match the viewed intervertebral space, or which the surgeon may select in an even progression of the use of a set of rasps 451 to complete the preparation of the intervertebral space for implantation. Referring to Table 1, below, a matrix of the preferred size combinations of one side of the rasps 451 is shown.

TABLE 1

| DIAMETER DIMENSION "fff", in centimeters | | | | |
|---|---|---|---|---|
| WIDTH | — | 18 | 23 | 28 |
| DIMENSION | 6 | X | X | X |
| "hhh" in | 8 | X | X | X |
| centimeters | 10 | X | X | X |
|  | 12 | X | X | X |
|  | 14 | X | X | X |

In the table above, the designator "X" refers to one instrument of a complete set which a surgeon should have available when performing the spinal implant procedure. Ideally the surgeon, once the spine is accessed, and once the box chisel 101 of FIG. 8 is used to quickly remove most of the cartilage material, can measure or visually evaluate the proper inter spinal width, or simply start with the smallest dimension peripheral rasp 451 which is shown in the table as having an eighteen centimeter diameter dimension "fff" and a six centimeter thickness, dimension "hhh". A visual and "feel" evaluation can enable the surgeon to intelligently and cautiously move to a next higher thickness or diameter. Because the peripheral rasp 451 have their total external surfaces exposed, sterilization should occur fully and easily. Going through several rasps within a matrixed kit, and which is preferably arranged as shown in the table, provides a cautious yet quickly adaptable and efficient method of finishing the preparation of the intervertebral area.

The view of FIG. 37 from the side is a mirror view with respect to the opposite side. Referring to FIG. 38, an end view looking into the posterior surface portion 475 illustrates a further difference of face surfaces 457 and 471. It is preferable for an indicator, such as an indicator arrow shown in FIG. 38 to be used to help the surgeon orient the peripheral rasp 451.

Referring to FIG. 39, a view looking into the anterior surface portion 477 is seen. Note that the shaft 459 is shown in section as it would otherwise be directed at the observer.

Now, as has been explained in detail, the rasp 451 has to be inserted into a wedge shaped intervertebral space in an orientation such that a posterior surface portion 475 having the small smooth area 482 directly or nearly directly faces the posterior of the wedge shaped intervertebral space, and also such that the anterior surface portion 477 faces the anterior of the wedge shaped intervertebral space. Thus it is clear that the peripheral rasp 451 of FIGS. 35–38 are intended for an anterior entry. To take the peripheral rasp 451 to enter anterolaterally, or at an angle displaced from a nearly straight in anterior entry is not recommended as there would be a mis-match in the orientation of the posterior surface portion 475 and the anterior surface portion 477, similar to that which would occur if the peripheral rasp 451 were angularly pivoted too far to one side or the other. The anterolateral entry into the intervertebral space may occur at an angle of up to 55° from a line taken straight in anterior to the intervertebral space. As a result, an intervertebral peripheral rasp which is used for an anterolateral approach should have its shaft 459 attached to extend radially at an angular displacement matching the approach of the anterolateral procedure's angular displacement from such a line taken straight in anterior to the intervertebral space. Again, where the upper and lower peripheral rasp surfaces are to differ in magnitude of curvature, an indication of such should be present.

Referring to FIG. 40, a left approach anterolateral procedure peripheral rasp 491 is seen in an upper perspective view, with the more curved surface 457 on top, and looking into the anterior surface portion 477. A location of missing shaft 459 is seen as it would have projected from the anterior surface portion 477 if it were peripheral rasp 451, and also to indicate the anterior axis. However, a left anterior rasp 491 has an identical shaft 493 which is displaced an angle of $\phi°$ to the right of missing shaft 459 or the anterior axis 459 for an instrument for performing a left anterior procedure. Referring to FIG. 41, and in the alternative, a right anterior rasp 495 an identical shaft 497 which is also displaced an angle of $\phi°$, but to the left of missing shaft 459 or the anterior axis 459 for an instrument for performing a right anterior procedure.

Referring to FIG. 42, an end view, along shaft 493, of the left approach anterolateral procedure rasp 491 is seen to illustrate the fact that the approach to the intervertebral space need not be accomplished with an instrument necessarily having a narrower leading edge, such as the posterior edge 475 seen in FIG. 37.

Figure 43:
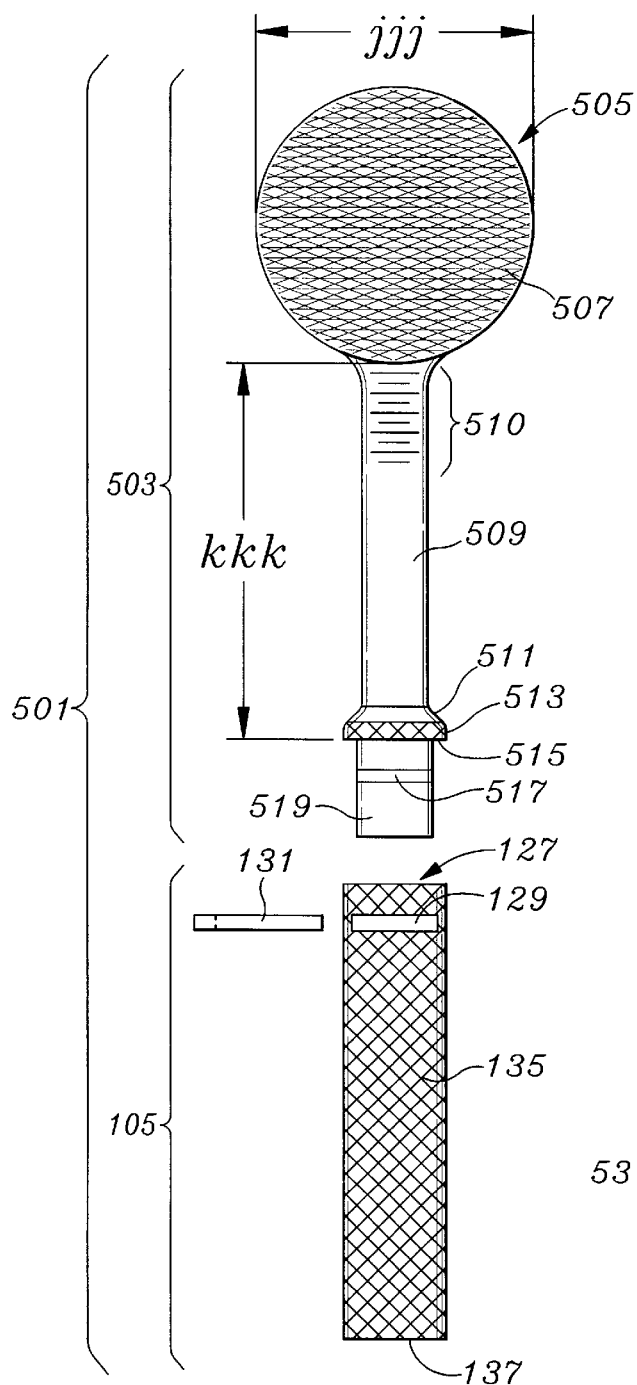
FIG. 43 is a plan view of an anterior type intervertebrally operated vertebral bone plate shaping rasp fitting the intervertebral area for safely removing material in from the bone plates immediately above and below the intervertebral space and which will reduce time and enhance safety for cartilage removal.

FIG. 43, an intervertebrally operated vertebral bone plate shaping rasp 501, is seen having an anatomical shape and for shaping the bone plates in an anatomically shaped way. The rasp 501 is inserted into the disc space to remove the remaining fibrocartilagenous material from the surfaces of the end plates and to shape the end space precisely to accommodate anatomically shaped implants, set forth in detail below. The rasp 501 also serves to "score" the end plates to provide greater surface and new bone growth area and more vascular surface to facilitate and promote fusion.

The handle portion 105, including its bore 127, open slot 129, locking ring 131, groove 133, burled surface 135, butt end 137 and the dimensions of the handle portion 105 are as was shown in FIG. 8. A rasp insert portion 503 includes a head portion 505 which has a circular shape as seen from the perspective of FIG. 43. A rasp surface 507 of crossing grooves may be arranged in any pattern. The circular side of the head portion 505 blends into a shaft 509. At the end of the shaft 509 is an expanded portion 511 having a burled surface 513 adjacent a radial surface 515. A groove 517 on an insertion member 519 operates in conjunction with the locking ring 131 seen in FIG. 8.

The dimensions seen for the rasp 501 of FIG. 43 include a diameter dimension "jjj" which may preferably be the same in all directions. The actual dimensions for the diameter of the rasp 501 will be seen to be a part of a system and are thus included in a table below. A dimension "kkk" is shown as the length of the shaft 509 and may preferably be from about 10 to about 20 centimeters in length.

Figure 44:
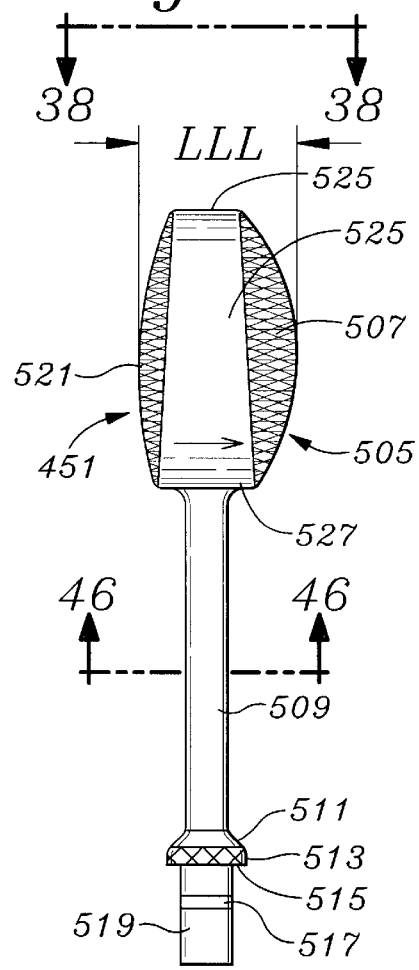
FIG. 44 is a side view of the intervertebrally operated vertebral bone plate shaping rasp of FIG. 43 and illustrating the different curvature of the two sides facing the bone plates of the spine.

Referring to FIG. 44, a side view of the intervertebral rasp 501 of FIG. 35 illustrates the shape orientation for an anterior procedure, where the rasp 501 is brought from a position anterior to the spinal column and moved in the posterior direction into the intervertebral space. As can be seen, in addition to the rasp surface 507, a rasp surface 521 is oppositely disposed with respect to the rasp surface 507.

The rasp surface 521 may be of a lesser curvature than the rasp surface 507 where the rasp is to be even more specifically shaped for orientation within the intervertebral space. In the typical intervertebral space, each vertebral bone has an upper directed surface which is relatively less curved, and a downwardly directed surface which is relatively more curved. In the side view of FIG. 44, and although it may be somewhat exaggerated for viewabilty, the rasp surface 521 is relatively less curved and would engage a lower spinal bone surface while the rasp surface 507 would engage a relatively more curved upper spinal bone plate. This subtle difference is illustrated for as an example of the most customized rasp instrument possible. As was the case for the peripheral rasp 451, the difference in curvature is a complex function of the shape as the surfaces are not radiused surfaces and perhaps may be described as a ratio of center height to a height taken at half of the radius to give a simple example of how the two sides may differ.

The two rasp surfaces 521 and 507 may be exactly alike in an advantageous, but slightly less than optimal realization. The rasp motion for removal of cartilage material from the bone plate will, like that for rasp 451, consist of movement of the shaft 459 to the left and right in FIG. 43 or in a direction into and out of the paper, of insertion member 519, as seen in FIG. 44. Angular motion will generally be restricted due not only to the presence of viscera at the entrance to the intervertebral space, but also due to the fact that the posterior surface portion 525 has a narrow height and that the anterior surface portion 527 has a wide height and that too much angular displacement would cause improper operation as by binding and mismatch with the naturally occurring intervertebral bone surfaces.

The surface between the rasp surfaces 507 and 521 is generally cylindrical but enables the rasp surfaces 507 and 521 to be angled slightly apart from each other in accord with the anatomical angular displacement of the intervertebral surfaces. The surrounding surface of the rasp 501 between the rasp surfaces 507 and 521 has a minimum extent between the rasp surfaces 507 and 521 at a posterior surface portion 525. The shaft 519 attaches to the head portion 505 at a maximum extent between the rasp surfaces 507 and 521 at an anterior surface portion 527 irrespective of the fact that the shaft 509 is present.

Measured with respect to an individual's spine, and looking from the posterior surface toward the anterior surface, a surface having a medium extent of separation between the rasp surfaces 507 and 521 at a left side surface portion 529 is shown. A right side surface portion 531 is indicated by an arrow leading to the rear of the rasp 501 seen in FIG. 44. Since left side surface portion 529 is in transition between the minimum separation posterior surface portion 525 and maximum separation anterior surface portion 527, the left side surface portion 529 at its mid point appears somewhat wedge shaped because it is in transition between minimum separation posterior surface portion 525 and maximum separation anterior surface portion 527. The mid points of the minimum separation posterior surface portion 525 and maximum separation anterior surface portion 527 approach parallel side edge relationship at their points of minima and maxima, respectively.

The thickness between either the maximum outer dimension of the rasp surface 521 or the concentric center of its diameter may differ very little. As can be seen in FIG. 44 the surfaces 507 and 521 may be even surfaces and may rise evenly from the transition between surfaces 507 or 521 and the surfaces 527, 529, or 525. As such, the surfaces 507 and 521 may appear to be very slightly inclined toward each other. The dimension "LLL" is seen to be a maximum or near maximum width dimension between the two general maxima of each of the rasp surfaces 507 and 521. It is this dimension "LLL" which the surgeon may select in a set of rasps 501 to either match the viewed intervertebral space, or which the surgeon may select in an even progression of the use of a set of rasps 501 to complete the preparation of the intervertebral space for implantation. Referring to Table 2, below, a matrix of the preferred size combinations of one side of the rasps 501 is shown.

TABLE 2

| | DIAMETER DIMENSION "jjj", in centimeters | | | |
|---|---|---|---|---|
| WIDTH | — | 20 | 25 | 30 |
| DIMENSION | 7 | X | X | X |
| "hhh" in | 9 | X | X | X |
| | 11 | X | X | X |
| centimeters | 13 | X | X | X |
| | 15 | X | X | X |

In the table above, the designator "X" refers to a tool of a complete set which a surgeon should have available when performing the spinal implant procedure. Note that the dimensions of Table 2 are about 3 millimeters less in diameter than dimensions for the peripheral rasp 451. Ideally the surgeon, once the spine is accessed, and once the box chisel 101 of FIG. 8 is used to quickly remove most of the cartilage material, can measure or visually evaluate the proper inter spinal width, or simply start with the smallest dimension rasp which is shown in the table as having a twenty centimeter diameter dimension "jjj" and a seven centimeter thickness, dimension "LLL". A visual and "feel" evaluation can enable the surgeon to intelligently and cautiously move to a next higher thickness or diameter. Because the rasps 501 have total external surfaces exposed, sterilization should occur fully and easily. Going through several rasps 501 within a matrixed kit, and which is preferably arranged as shown in the table, provides a cautious yet quickly adaptable and efficient method of finishing the preparation of the intervertebral area.

Figure 45:
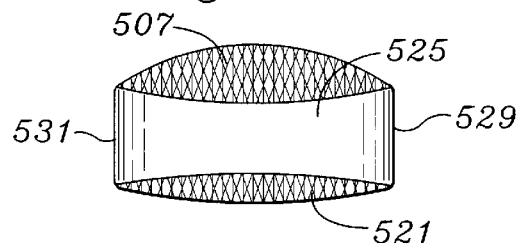
FIG. 45 is an end view of the intervertebrally operated vertebral bone plate shaping rasp at a side opposite the shaft.

The view of FIG. 44 from the side is a mirror view with respect to the opposite side. Referring to FIG. 45, an end view looking into the posterior surface portion 525 illustrates a further difference of rasp surfaces 507 and 521. It is preferable for an indicator, such as an indicator arrow shown in FIG. 45 to be used to help the surgeon orient the rasp 501.

Referring to FIG. 46, a view looking into the anterior surface portion 527 is seen. Note that the shaft 509 is shown in section as it would otherwise be directed at the observer.

Now, as has been explained in detail, the rasp 501 has to be inserted into a wedge shaped intervertebral space in an orientation such that a posterior surface portion 525 directly or nearly directly faces the posterior of the wedge shaped intervertebral space, and also such that the anterior surface portion 527 faces the anterior of the wedge shaped intervertebral space. Thus it is clear that the rasp of FIGS. 43–49 are intended for an anterior entry. Similar to the principles set forth for rasp 451, to take the rasp 501 and to enter anterolaterally is not recommended as there would be a mis-match in the orientation of the posterior surface portion 525 and the anterior surface portion 527, similar to that which would occur if the rasp 501 were angularly pivoted too far to one side or the other. The anterolateral entry into the intervertebral space may occur at an angle of up to 55° from a line taken straight in anterior to the intervertebral space. As a result, an intervertebral rasp which is used for an anterolateral approach should have its shaft 509 attached to extend radially at an angular displacement matching the approach of the anterolateral procedure's angular displacement from such a line taken straight in anterior to the intervertebral space. Again, where the upper and lower rasp surfaces are to differ in magnitude of curvature, an indication of such should be present.

Referring to FIG. 47, a left approach anterolateral procedure rasp 541 is seen in an upper perspective view, with the more curved surface 507 on top, and looking into the anterior surface portion 527. A location of missing shaft 509 is seen as it would have projected from the anterior surface portion 527 if it were rasp 501, and also to indicate the anterior axis. However, a left anterior rasp 541 has an identical shaft 543 which is displaced an angle of φ° to the right of missing shaft 509 or the anterior axis 509 for an instrument for performing a left anterior procedure. In the alternative, a right anterior rasp 545 has an identical shaft 547 which is also displaced an angle of φ°, but to the left of missing shaft 509 or the anterior axis 509 for an instrument for performing a right anterior procedure.

Figure 49:
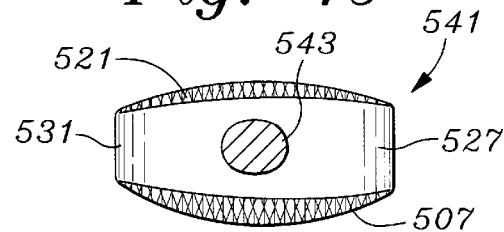
FIG. 49 is an end view of the left approach anterolateral procedure intervertebrally operated vertebral bone plate shaping rasp looking into the shaft.

Referring to FIG. 49, an end view, along shaft 543, of the left approach anterolateral procedure rasp 541 is seen to illustrate the fact that the approach to the intervertebral space need not be accomplished with an instrument necessarily having a narrower leading edge, such as the posterior edge 525 seen in FIG. 44.

Referring to FIG. 50, one alternative, especially for the smaller sizes is to combine the face rasp surfaces 521 & 507 with the cylindrically peripheral rasp surface 458 to form a preferably smaller roughing combination rasp 551, which also has an anatomical shape. The combination rasp 551 will preferably have a size construct similar to that for peripheral rasp 451 and may be used immediately after the box chisel 101 of FIG. 8 is used to quickly remove most of the cartilage, especially if the roughness of the rasp face is relatively great. Where the roughness is not great, it can be used possibly in place of the rasps 451 and 501 in circumstances where a combination tool is permissible. This combination rasp is preferably available in the smallest size and is simply used to only begin to attain a shape in the intervertebral space and immediately after the box chisel 101 has left a relatively rectangular opening. Other components of the combination rasp 551 will preferably remain as described in FIGS. 35–49. Where the rasp 551 is used to complete the preparation of the intervertebral disc space, all of the goals and advantages stated separately for each of the rasps 451 and 501 are achievable with the rasp 551.

In terms of standardization, we have described tools which are used to, in a custom fashion, smooth and shape the intervertebral space, both the side walls typically bound by cartilage and the upper and lower bone plates. Further, the instruments, including rasps 451 and 501 and their anterolateral variations rasps 491, 495, 541, & 545 can have face surfaces which are customized to take advantage of the different curvature of the surfaces between the bone plates. Such high customization can lead to further customization in both measurement of the intervertebral space and selection of implant components so as to avoid undue time in custom shaping, etc.

Figure 51:
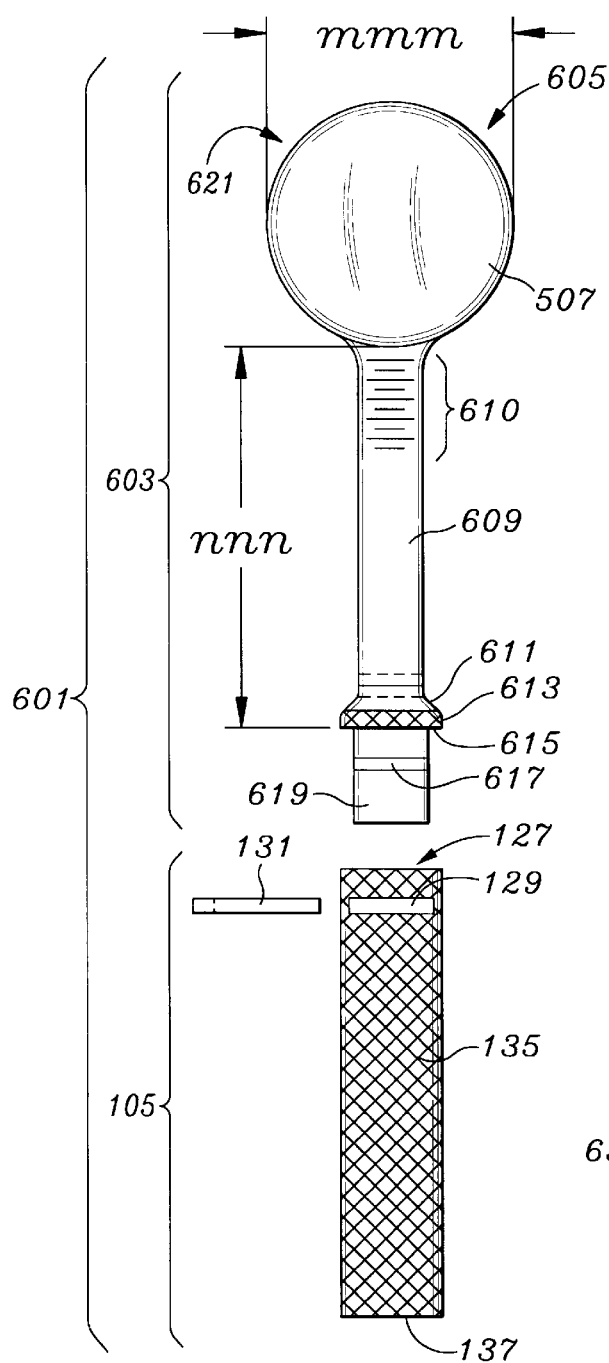
FIG. 51 is a plan view of an anatomically shaped intervertebral sizing tool fitting the intervertebral area for safely gauging the depth of material removed, magnitude of the intervertebral space between vertebra and diameter of the removed cartilage material and which will reduce time, enhance safety, and eliminate both mismatch of implant material selected as well as the necessity of having to custom shape the implant material.

Referring to FIG. 51, an anatomically shaped intervertebral sizing tool 601 is seen is seen. The intervertebral sizing tool is a sizer for the disc space formed by the rasps 451 and 501, and is utilized to determine the proper size of bone implant to provide optimum annular ligamentaxis tension. This "ligamentaxis" is critical to maintain stability of the bone implant and to promote bony fusion between the vertebral end plates and the bone graft. During the sizing procedure, the distractors 31 are removed to give a "true" feel of the tension and force exerted by the adjacent vertebral bone plates. The bone grafts utilizable in conjunction with the intervertebral sizing tool 601 include femoral allograft bone, either fresh frozen or prepared by freeze drying. In the alternative the femoral allograft bone can be made from synthetic materials or even xenograft material.

The handle portion 105, including its bore 127, open slot 129, locking ring 131, groove 133, burled surface 135, butt end 137 and the dimensions of the handle portion 105 are as was shown in FIG. 8 in order to complete an interchangeable set of all instruments in the present inventive system and method. An insertion sizer 603 includes a head portion 605 which has a circular shape as seen from the perspective of FIG. 51. A smooth surface 607 is seen and may be more severely curved than an opposite surface. The circular extent of the head portion 605 blends into a shaft 609. Shaft 609, at the point of connection to the circular side of the head portion 605, includes a scale 610 which shows numbering measured from the farthest point of the other side of the head portion 605, so that the surgeon will be able to accurately judge that the insertion sizer 603 being used for size measurement has reached the proper extent of the intervertebral space. If the surgeon has used the rasps 451, 501, 551, the surgeon knows the physical depth at which work has occurred and will typically match this depth with the scale 610 to make quickly and absolutely certain that the insertion sizer 603 is in a proper position to enable the surgeon to judge that the true dimensions of the intervertebral space match those of the insertion sizer 603.

At the end of the shaft 609 is an expanded portion 611 having a burled surface 613 adjacent a radial surface 615. A groove 617 on an insertion member 619 operates in conjunction with the locking ring 131 seen in FIG. 8. A view of the end of the handle 105 is the same as was seen in FIG. 36 and would also reveal the oval nature of the handle portion 105.

The dimensions seen for the sizing tool 601 of FIG. 43 include a diameter dimension "mmm" which may preferably be the same in all directions. The actual dimensions for the diameter of the sizing tool 601 will be seen to be a part of a system and are thus included in a table below and will be seen to be slightly different from the dimensions given for the rasp 451 and the rasp 501. A dimension "nnn" is shown as the length of the shaft 609 and may preferably be from about 10 to about 20 centimeters in length.

Figure 52:
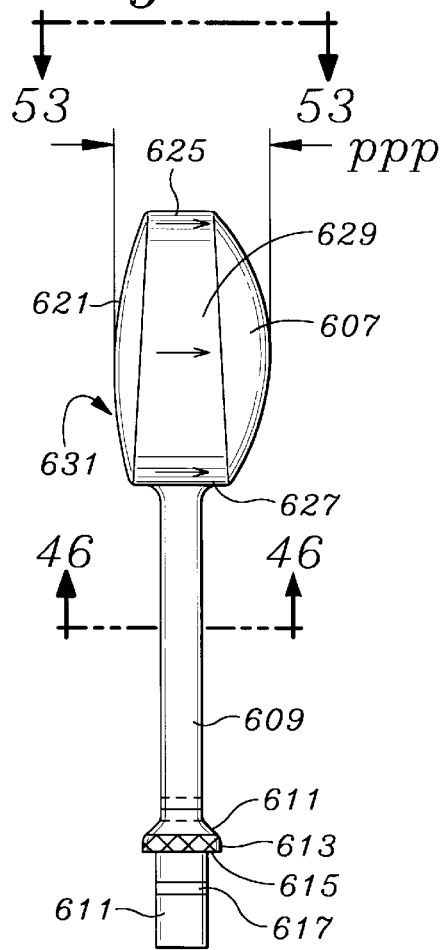
FIG. 52 is a side view of the anatomically shaped intervertebral sizing tool of FIG. 51 and illustrating the different curvature of the two sides facing the bone plates of the spine.

Referring to FIG. 52, a side view of the intervertebral sizing tool 601 of FIG. 51 illustrates the shape orientation for an anterior procedure, where the sizing tool 601 is brought from a position anterior to the spinal column and moved in the posterior direction into the intervertebral space, as was the case for the rasp 451 insert portion 453 and rasp 501 insert portion 503. As can be seen, in addition to the smooth surface 607, a smooth surface 621 is oppositely disposed with respect to the smooth surface 607.

Again, the smooth surface 621 may be of a lesser curvature than the smooth surface 607 where the intervertebral sizing tool 601 is to be even more specifically shaped for orientation within the intervertebral space. In the typical intervertebral space, each vertebral bone has an upper directed surface which is relatively less curved, and a downwardly directed surface which is relatively more curved. In the side view of FIG. 52, and although it may be somewhat exaggerated for viewabilty, the smooth surface 621 is relatively less curved and would engage a lower spinal bone surface while the smooth surface 607 would engage a relatively more curved upper spinal bone plate. This subtle difference is illustrated for as an example of the most customized sizing tool 601 possible. The difference in curvature is a complex function, and may be the same as was the case for the rasps 451, 501 or 551, or the shape for the intervertebral sizing tool 601 may be made to provide a more accurate gauge of the size of the intervertebral space. In some cases, the contour of the intervertebral sizing tool 601 may be sized to correspond to different types of implants. By way of example only, where an implant is extremely hard, the contour of the intervertebral sizing tool 601 may be sized to match it exactly. Where the implant is more deformable, the contour of the intervertebral sizing tool 601 may be sized to a shape which the implant will assume once placed in compression between the intervertebral bone plates. As before, and including these additional possibilities, the shape of the intervertebral sizing tool 601 is highly customizable.

The two smooth surfaces 621 and 607 may be exactly alike in an advantageous, but slightly less than optimal realization. The motion for measurably sizing will consist of simple insertion of the intervertebral sizing tool 601, with only slight movement of the shaft 459 to the left and right to insure that the intervertebral sizing tool 601 is in its proper "seat" or comfortable fit within the intervertebral space. Again, angular motion will generally be restricted due not only to the presence of viscera at the entrance to the intervertebral space, but also because it is unnecessary for sizing.

However, the various different sized surfaces are also seen. A posterior surface portion 625 has a narrow height and an anterior surface portion 627 has a wide height. The surfaces between the smooth surfaces 607 and 621 is generally cylindrical but enables the smooth surfaces 607 and 621 to be angled slightly apart from each other in accord with the anatomical angular displacement of the intervertebral surfaces. The surrounding surface of the intervertebral sizing tool 601 insertion sizer 603 between the smooth surfaces 621 and 607 has a minimum extent between the surfaces 621 and 607 at a posterior surface portion 625. The shaft 609 attaches to the head portion 605 at a maximum extent between the smooth surfaces 621 and 607 at an anterior surface portion 627 irrespective of the fact that the shaft 609 is present.

Measured with respect to an individual's spine, and looking from the posterior surface toward the anterior surface, a surface having a medium extent of separation between the surfaces 607 and 621 at a left side surface portion 629 is shown. A right side surface portion 631 is indicated by an arrow leading to the rear of the insertion sizer 603 seen in FIG. 44. Since left side surface portion 629 is in transition between the minimum separation posterior surface portion 625 and maximum separation anterior surface portion 627, the left side surface portion 629 at its mid point appears somewhat wedge shaped because it is in transition between minimum separation posterior surface portion 625 and maximum separation anterior surface portion 627. The mid points of the minimum separation posterior surface portion 625 and maximum separation anterior surface portion 627 approach parallel side edge relationship at their points of minima and maxima, respectively. Note that arrows are placed to show the orientation, given that the surface 607 is shown to be different than surface 621, the arrows pointing upwardly to the more sharply curved upper plate of the vertebra.

The thickness between either the maximum outer dimension of the smooth surface 621 or the concentric center of its diameter may differ very little. As can be seen in FIG. 52 the surfaces 621 and 607 may be even surfaces and may rise evenly from the transition between surfaces 621 or 607 and the surfaces 627, 629, 631, or 625. As such, the surfaces 621 and 607 may appear to be very slightly inclined toward each other. The dimension "ppp" is seen to be a maximum or near maximum width dimension between the two general maxima of each of the smooth surfaces 607 and 621. It is this dimension "ppp" which the surgeon may select in a set of insertion sizers 603 following an appropriately sized rasp 451 to as accurately as possible gauge the rasped intervertebral space. The dimensions of the insertion sizer 603 will be related to closely, but different from the sizes of the rasp portion 453. One possibility for the preferred dimension is seen by referring to Table 3, below. A matrix of the preferred size combinations of the insertion sizer 603 is shown.

TABLE 3

| DIAMETER DIMENSION "mmm", in centimeters | | | | | Custom Height of Implant |
|---|---|---|---|---|---|
| WIDTH DIMENSION | — | 20 | 25 | 30 | |
| | 8 | X | X | X | 9 |

TABLE 3-continued

| DIAMETER DIMENSION "mmm", in centimeters | | | | | Custom Height of Implant |
|---|---|---|---|---|---|
| "ppp" in centimeters | 10 | X | X | X | 11 |
| | 12 | X | X | X | 13 |
| | 14 | X | X | X | 15 |
| | 16 | X | X | X | 17 |

In the table above, the designator "X" refers to a tool of a complete set which a surgeon should have available when performing the spinal implant procedure, as well as a corresponding thickness of implant matching the DIAMETER DIMENSION "mmm", in centimeters and which is seen as being generally always one millimeter greater than the thickness of the corresponding insertion sizer 603. Again, this difference may differ to a greater or lesser degree based upon the material chosen. As can be seen in comparison, the thickness between the surfaces 507 and 521 of the insertion sizer 603 is one millimeter, in general, greater than the thickness or height between rasp surfaces 471 and 457 of the rasp 451, or between the face surfaces 521 and 507 of the rasp 501 but one millimeter less than the thickness of the implant. Ideally the surgeon, once the spine is accessed, and once the box chisel 101 of FIG. 8 is used to quickly remove most of the cartilage material, once the rasp action is performed, can use the insertion sizer 603 to evaluate the proper inter spinal width corresponding to a given size implant.

Figure 53:
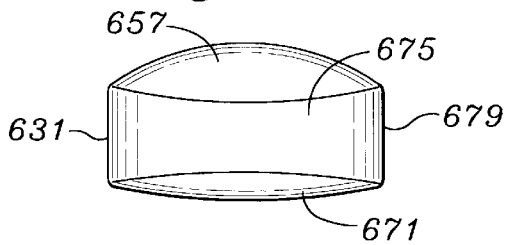
FIG. 53 is an end view of the anatomically shaped intervertebral sizing tool at a side opposite the shaft.

The view of FIG. 52 from the side is a mirror view with respect to the opposite side. Referring to FIG. 53, an end view looking into the posterior surface portion 675 illustrates a further difference of surfaces 607 and 621. It is preferable for an indicator, such as an indicator arrow shown in FIG. 53 to be used to help the surgeon orient the insertion sizer 603.

Referring to FIG. 54, a view looking into the anterior surface portion 627 is seen. Note that the shaft 609 is shown in section as it would otherwise be directed at the observer.

Now, as has been explained in detail, the insertion sizer 603 has to be inserted into a wedge shaped intervertebral space in an orientation such that a posterior surface portion 675 directly or nearly directly faces the posterior of the wedge shaped intervertebral space, and also such that the anterior surface portion 627 faces the anterior of the wedge shaped intervertebral space. Thus it is clear that the insertion sizer 603 of FIGS. 51–54 are intended for an anterior entry. To have taken the insertion sizer 603 to enter anterolaterally is, much like the rasps 451 and 501, not recommended as there would be a mis-match in the orientation of the posterior surface portion 675 and the anterior surface portion 627. As a result, an intervertebral insertion sizer 603 which is used for an anterolateral approach should have its shaft 459 attached to extend radially at an angular displacement matching the approach of the anterolateral procedure's angular displacement from such a line taken straight in anterior to the intervertebral space. Again, this is seen in FIGS. 55 and 56, where the upper and lower smooth surfaces 607 and 621 differ in magnitude of curvature. FIG. 55 illustrates a left approach anterolateral intervertebral sizing tool 691 with the more curved surface 657 on top, and looking into the anterior surface portion 627. A location of missing shaft 659 is seen as it would have projected from the anterior surface portion 627 and also to indicate the anterior axis. The left anterior intervertebral sizing tool 691 has an identical shaft 693 which is displaced an angle of $\phi°$ to the right of missing shaft 659 or the anterior axis 659 for an instrument for performing a left anterior procedure. In the alternative, a right anterior intervertebral sizing tool 695 has an identical shaft 697 which is also displaced an angle of $\phi°$, but to the left of missing shaft 659 or the anterior axis 659 for an instrument for performing a right anterior procedure.

Figure 57:
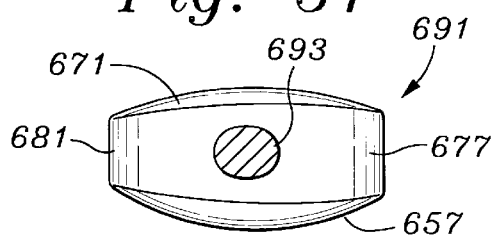
FIG. 57 is an end view of the left approach anterolateral procedure anatomically shaped intervertebral sizing tool looking into the shaft.

Referring to FIG. 57, an end view, along shaft 693, of the left approach anterolateral intervertebral sizing tool 691 is seen to illustrate the fact that the approach to the intervertebral space need not be accomplished with an instrument necessarily having a narrower leading edge.

A femoral ring bone implant, similar to femoral ring bone implant 201 and following the sizing and shape system described for the rasps 451 and 501 and intervertebral sizing tool 601 for the anterior approach will be seen, and followed by some modifications for the anterolateral approach taking to account some angle shifting as was seen for rasps 491, 495, 541 and 545.

Figure 58:
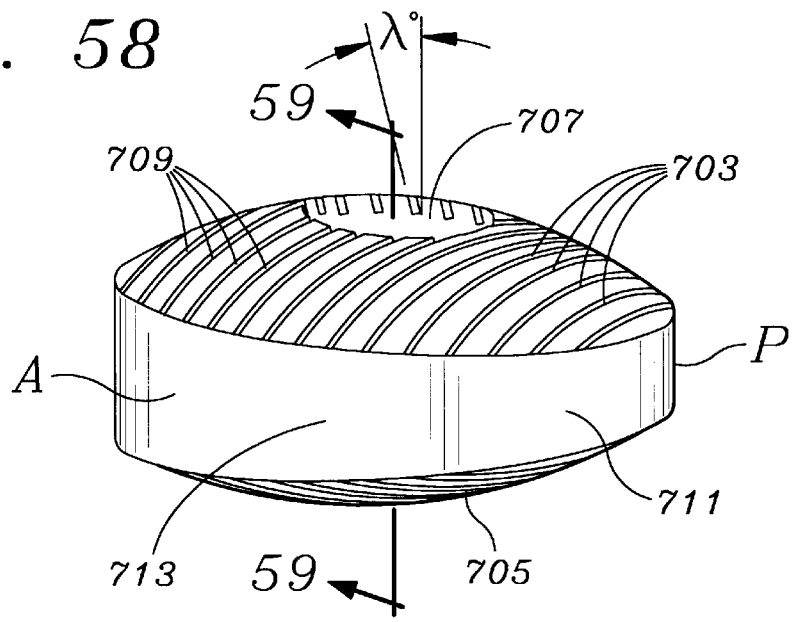
FIG. 58 illustrates a femoral ring bone implant is configured for an anterior approach insertion, and is shown in side sectional view.

Referring to FIG. 58, a femoral ring bone implant 701, configured for an anterior approach insertion, is shown in side sectional view. The posterior end of the femoral ring bone implant 701 is shown by a "P" reference, while the anterior end is shown by an "A" reference. A top surface 703 is generally more severely rounded than a lower surface 705 to account for the more rounded nature of the upper bone plate of the spine than the less rounded nature of the lower bone plate of the spine. The curvature of the upper and lower surfaces 703 and 705 will ideally bear a relationship to the curvature of the upper and lower surfaces of the rasps 501. Also shown in the femoral ring bone implant 701 is a central opening 707.

The upper and lower surfaces 703 and 705 contain a series of preferably evenly spaced line slots 709, shown more prominently on the upper surface 703 due to the angle of the perspective, and which extend generally perpendicular to a line between the posterior end "P" and anterior end "A". Notice also that the slots 709 may, but preferably do not extend straight down into the upper surface 703, but are angled to open toward the posterior end, similar to that seen for implant 201, by an angle of $\lambda°$ which has an angular magnitude from about fifty degrees to about seventy degrees from plane normal to a general extent or averaged extent of their respective upper or lower surfaces 703 and 705.

The line slots 709, preferably combined with the angling toward the posterior end "P" accomplishes several objectives. First, it causes the femoral ring bone implant 701 to be easier to insert into the intervertebral space. To the extent that the upper or lower surfaces 703 and 705 have to "give" or "deflect" to assist in entry of the femoral ring bone implant 701 past the intervertebral space entrance. Second, once the femoral ring bone implant 701, the line slots 709 cause the amounts of femoral ring bone implant 701 material between them to acts as load flanking members against the upper and lower bone plates of the intervertebral space into which they are placed to more securely prevent outward removal of the femoral ring bone implant 701 from the intervertebral space especially given that an opening was made and that in the anterior procedure the lordosis is directed toward such anterior opening. Third, the additional surface area of the upper and/or lower surfaces 703 and 705 provide additional area for promoting bone growth. Not only is additional area provided, but additional space as well. Bone growth from the upper and lower plates face no resistance to growth within the line slots 709 of the femoral ring bone implant 701. Although it is true that no resistance will be hand to bone growth from the bone plates of the spine into the central opening 707, the most stabilizing growth is within the line slots 709 since less bone has to grow to create a positive lock against any forces tending to expel the femoral ring bone implant 701 from an intervertebral space having a natural angle of lordosis as previously described.

Femoral ring bone implant 701 also has a generally cylindrical outer surface 711 which narrows to a minimum width at the posterior or "P" side of the implant 701 and which broadens to a maximum width at the anterior or "A" side of the implant 701. In the anterior approach, the "P" side of the implant 701 is inserted as a leading edge into the intervertebral space. Once the implant 701 is seated, the "P" side of the implant 701 will face, within the intervertebral space, in the direction of the spinal chord, while the "A" side of the implant 701 will face directly anteriorly, and thus face away from the spinal chord and outward toward the front of the patient. In other approaches, the end of the implant 701 entering into the intervertebral will deviate from the "P" end, but the final position of the implant 701 will always be such that the "P" of the implant side of the implant 701 will face, within the intervertebral space, in the direction of the spinal chord. Further, the line slots 709 may also have their orientation changed with a line normal to the slots 709 altered from alignment with a line between the "A" and "P" ends, to continue the above advantages of (1) easier insertion into the intervertebral space especially to the extent that any deflection is present, (2) the existence of femoral ring bone implant 701 material between the line slots to acts as load flanking members to more securely prevent outward removal of the femoral ring bone implant 701 from the intervertebral space, especially in the direction of the opening formed, even though the natural lordosis and such opening are not in alignment, and (3) to promote bone growth from the upper and lower plates within the line slots 709. Implants for insertion by procedures having an angular relationship to the anterior procedure will be seen to simply involve a shifting of the angle of extension of the line slots 709 with regard to the "P" and "A" sides of the implant 701. To further register the orientation of the implant 701, from the posterior side looking forward, a left side 713, mid way between the ends "P" and "A" is seen.

Figure 59:
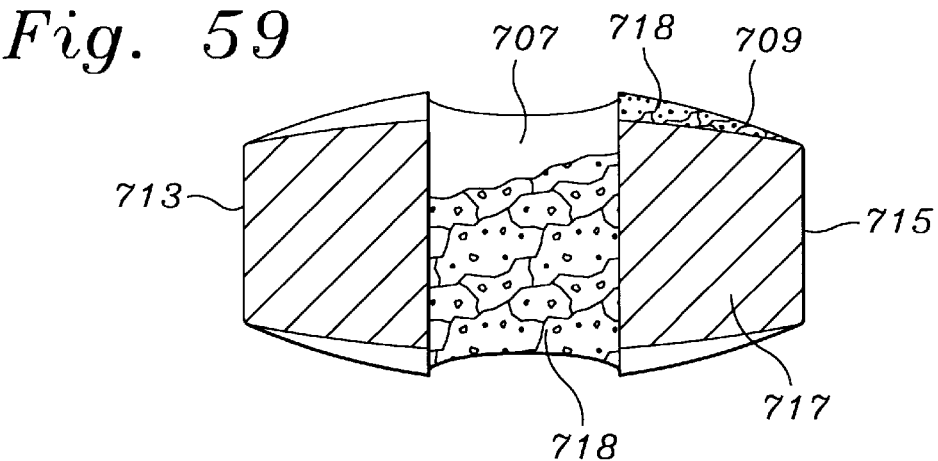

Continuing with a description of the implant 701, FIG. 59 is a sectional view looking toward anterior end "A". Opposite the left side 713, a right side 715 is now seen. The implant 701 has a generally toroidal extent shaped mass of bone tissue 717.

The central opening 707 may be packed with a material seen as material 718 which may be one of several combinations of materials and structures. Material 718 is also shown within the slot 709. Material 718 may be a collagen sponge or other substance, saturated with a bone morphogenetic protein substance, demineralized bone matrix prepared substance or other bone growth substance to promote even more rapid fixating bone growth. In addition, material 718 may be autogenous bone, typically harvested from the iliac crest of a patient undergoing the implant procedure. Further, material 718 may be any combination of structure or substance, now existing or discovered in future which promotes bone growth. Although the human harvested allograft structure is supplied with the a single pre-existing bore or aperture, a manufactured implant such as implant 201, 210, 214, 216, 295 or 701 can either (1) have a series of bores into which the bone morphogenetic protein or demineralized bone matrix prepared substance or autogenous bone can be introduced to facilitate growth, (2) have other facilitating structure into which the bone morphogenetic protein or demineralized bone matrix prepared substance or autogenous bone can be introduced, or (3) be manufactured as an integrated structure with the into which the bone morphogenetic protein or other substance can be pre-set for timed release or for invasive displacement from the implant structure.

As section 59—59 is taken along the base of two of the line slots 709, one from the top surface 703 and one from the bottom surface 705, the inside walls of such line slots 709 are readily seen.

Figure 60:
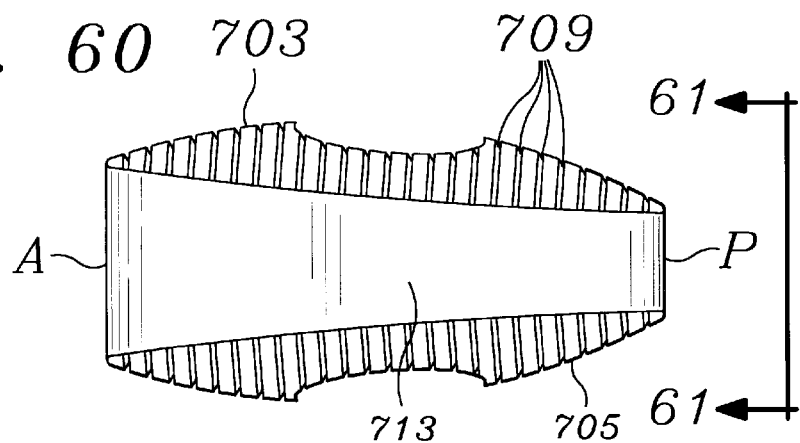
FIG. 60 illustrates a side view of the implant in order to illustrate the greater magnitude height of the upper surface, and what visually appears to be a wedge shape looking into its left side.
Figure 61:
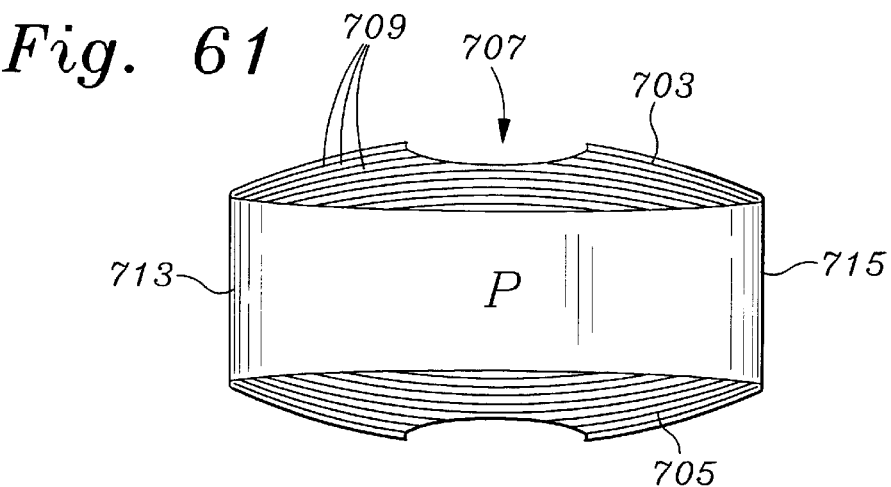
FIG. 61 illustrates a view taken along line 61—61 of FIG. 60 looking directly into the posterior side of the implant.

Referring to FIG. 60, a side view of the implant 701 is seen in order to illustrate the greater magnitude height of the upper surface 703, and what visually appears to be a wedge shape looking into left side 713. Referring to FIG. 61, a view taken along line 61—61 of FIG. 60 looks directly into the posterior side of the implant 701.

The changes to implant 701 to facilitate anterolateral approaches will change the orientation of the line grooves 709 so that the approach into the intervertebral space will still occur at right angles to the extent of the line grooves 709, but with the posterior end "P", anterior end "A" and left and right sides 713 and 715 still oriented properly as such an implant enters the intervertebral space prepared by the instruments of the invention. We have seen the angle φ as representative of the angular divergence from a straight anterior approach. For example, where φ° represents an angular divergence of about 45° from the straight anterior approach, the linear orientation and load flanking of the line grooves 709 will angularly rotate this same amount. The magnitude of 45° is chosen for illustration purposes only and to insure that enough difference is illustrated so that it can be visually gauged.

Figure 62:
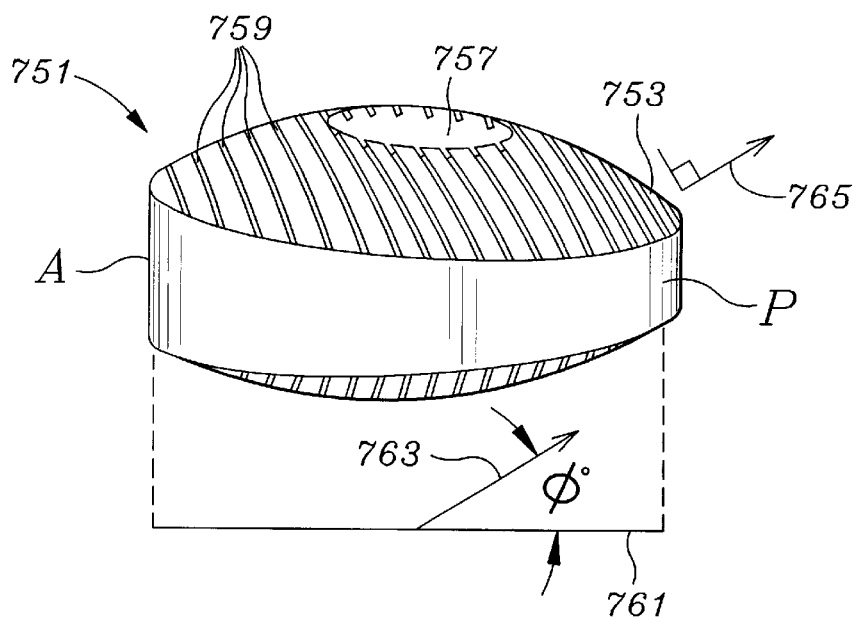
FIG. 62 is a perspective of an implant a femoral ring bone implant configured for an anterolateral approach insertion shown in side sectional view in exactly the same orientation with regard to its posterior "P" side, anterior "A" side as was seen for implant FIG. 58, and with arrows showing the angle of insertion.

Referring to FIG. 62, a perspective of an implant a femoral ring bone implant 751, configured for an anterolateral approach insertion, is shown in side sectional view in exactly the same orientation with regard to its posterior "P" side, anterior "A" side as was seen for implant 701 as it was shown in FIG. 58. Implant 751 has an upper surface 753, lower surface 755, and central opening 757. However, a series of preferably evenly spaced line slots 759 which are at an angle of 45° with respect to a line between the posterior end "P" of the implant 751 and the anterior end "A" of the implant 751.

A straight line 761 is seen below the implant 751 displaced downwardly by vertical dashed lines in order to show the front to back or anterior to posterior orientation of the implant 751. A line normal to the extent of the line slots 759 is also vertically dropped to the line 761 and seen as an arrowed line 763. A second arrowed line 765 extends from the implant 751, and which is parallel to arrowed line 763, and illustrates the direction of insertion of the implant 751 and as can be seen this direction 751 is normal or right angled to the linear extent of the line slots 759. In this configuration, the line slots 759 are oriented to facilitate insertion and to load flank against removal from a direction opposite to the insertion direction. The angle φ is shown to indicate the angularity of the line slots 759 with respect to line 761, and to emphasize that the orientation of the line slots 759 can be chosen for any degree of angular insertion deviating from anterior.

Figure 63:
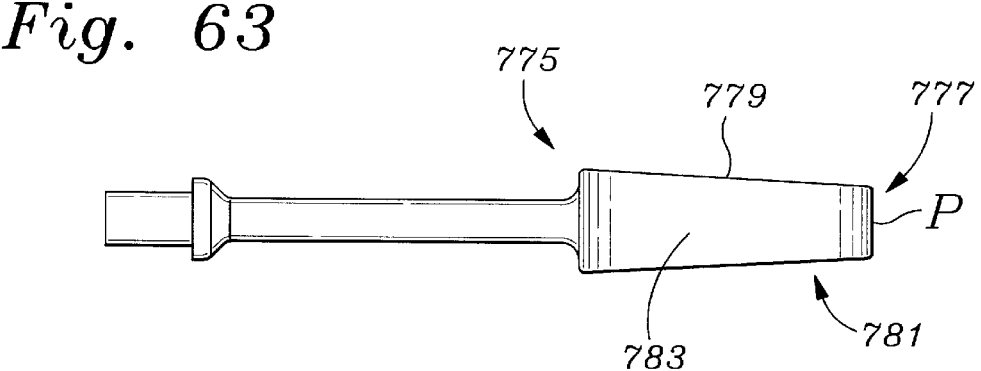
FIG. 63 illustrates a sizing tool having flat face surfaces which match and which is for use with the implant of FIGS. 16–18.

The intervertebral sizing tool 601 seen in FIGS. 51–57 has a shape matching the shape of the anatomical implant 701. Referring to FIG. 63, the implant 201 of FIGS. 16–18 can also have an associated set of sizing tools, such as a sizing tool 775 having a head portion 777 having an upper flat surface 779 and a lower flat surface 781. A side surface 783 is seen tapering toward a posterior end "P". Again, by matching the shape of the implant to be used with the shape of the intervertebral sizing tool 775, a good intervertebral fit can be more precisely achieved. The intervertebral sizing tool 775 is anatomical to the extent that its upper and lower surfaces 779 and 781 are angled to the extent of human lordosis expected between two adjacent spinal plates. So, from the flat matching surfaces of the intervertebral sizing tool 775 to the differentially curved intervertebral sizing tool 601, and all of the possibilities in between, it is possible to match any implant to any sizing tool 601, 775. Further, some shape variations in the rasps 451, 491, 495, 501, 541, and 545 are possible in order to provide a better match to a given implant of a given shape.

The distractors 31 can be a re-applied to allow easier insertion of any bone graft described herein and to retract the blood vessels. Even with precision preparation of the intervertebral disc space, and insertion of properly sized and shaped bone grafts, there will be cases when additional stability of the spine could be desirable. All of the structures and procedures described herein are compatible with the further use of plates and screws to additionally assist the "locking" of the graft into the intervertebral space. This can be done safely providing adequate structure is provided to insure that the plate material is compatible with the interbody environment and that none of the fixation structures will become dislodged. Other structures can enhance the described procedures and structures in the invention described herein.

While the present invention has been described in terms of a system of instruments and procedures for facilitating the performance of a spine fusion procedure, one skilled in the art will realize that the structure and techniques of the present invention can be applied to many appliances including any appliance which utilizes the embodiments of the instrumentation of the invention or any process which utilizes the steps of the invention.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A rasp for use in spine surgery comprising:
   a head portion for fitting within an intervertebral space between two adjacent vertebral bone plates and having an upper face and a lower face and an outwardly disposed surface extending between said upper and said lower face, and wherein at least a portion of one of said upper face, said lower face and said outwardly disposed surface includes a rasp surface;
   a shaft extending from said outwardly disposed surface to permit said head portion to be angularly displaced at least slightly within said intervertebral space; and
   a measuring scale on said shaft for indicating a depth of said head portion within said intervertebral space.

2. The rasp as recited in claim 1 and wherein said outwardly disposed surface has a maximum dimension extending between said upper and said lower face at an anterior side of said head portion and a minimum dimension extending between said upper and said lower face at a posterior side of said head portion, to account for a natural lordosis in said intervertebral space between two adjacent vertebral bone plates.

3. The rasp as recited in claim 2 wherein said shaft extends from said head portion substantially collinear with a longitudinal axis extending from said posterior side of said head portion to thereby form an anterior procedure rasp.

4. The rasp as recited in claim 2 wherein said shaft extends from said head portion at an angle with respect to a longitudinal axis extending from said posterior side of said head portion to thereby form an anterolateral procedure rasp.

5. The rasp as recited in claim 4 wherein said angle from which said shaft extends from said head portion with respect to said longitudinal axis extending from said from said posterior side of said head portion is from about 20° to about 70°.

6. A rasp for use in spine surgery comprising:
   a head portion for fitting within an intervertebral space between two adjacent vertebral bone plates and having an upper face and a lower face and an outwardly disposed surface extending between said upper and said lower face, and wherein at least a portion of one of said upper face, said lower face and said outwardly disposed surface includes a rasp surface;
   a shaft extending from said outwardly disposed surface to permit said head portion to be angularly displaced at least slightly within said intervertebral space; and
   wherein said upper and said lower faces are convex for complementing a naturally biconcave intervertebral disc space.

7. The rasp as recited in claim 3 and wherein both said upper and said lower faces are convex said upper face has a more acute curvature than said lower face in order to more closely complement the natural biconcave intervertebral disc space in which an upper, downwardly directed bone plate has a greater concavity than a concavity of a lower, upwardly directed bone plate.

8. The rasp as recited in claim 6 wherein said rasp is an intervertebral cylindrically directed rasp having a rasp surface on at least a portion of said outwardly disposed surface and wherein said upper and said lower faces are substantially smooth.

9. The rasp as recited in claim 8 and further comprising a measuring scale on said shaft for indicating the depth of said head portion within said intervertebral space.

10. The rasp as recited in claim 8 and wherein said upper face has a more acute curvature than said lower face in order to more closely complement the natural intervertebral disc space in which the upper, downwardly directed bone plate has a greater concavity than the concavity of the lower, upwardly directed bone plate.

11. The rasp as recited in claim 8 and wherein said outwardly disposed surface has a maximum dimension extending between said upper and said lower face at an anterior side of said head portion and a minimum dimension extending between said upper and said lower face at a posterior side of said head portion, to account for the natural lordosis in said intervertebral space between two adjacent vertebral bone plates.

12. The rasp as recited in claim 11 wherein said shaft extends from said head portion substantially collinear with a line extending from said from said posterior side of said head portion to thereby form an anterior procedure rasp.

13. The rasp as recited in claim 11 wherein said shaft extends from said head portion at an angle with respect to a line extending from said from said posterior side of said head portion to thereby form an anterolateral procedure rasp.

14. The rasp as recited in claim 13 and wherein said outwardly disposed surface has a maximum dimension extending between said upper and said lower face at an anterior side of said head portion and a minimum dimension extending between said upper and said lower face at a posterior side of said head portion, to account for the natural lordosis in said intervertebral space between two adjacent vertebral bone plates.

15. The rasp as recited in claim 14 wherein said shaft extends from said head portion substantially collinear with a line extending from said from said posterior side of said head portion to thereby form an anterior procedure rasp.

16. The rasp as recited in claim 14 wherein said shaft extends from said head portion at an angle with respect to a line extending from said from said posterior side of said head portion to thereby form an anterolateral procedure rasp.

17. The rasp as recited in claim 8 and wherein said rasp has a small smooth area on said outwardly disposed surface at said posterior side of said head portion for providing interruption to said rasp surface so that the progression toward the posterior of the human spine will be mitigated.

18. The rasp as recited in claim 6 wherein said rasp is an intervertebrally operated vertebral bone plate shaping rasp having a rasp surface on at least a portion of at least one of said upper and said lower faces and wherein said outwardly disposed surface is substantially smooth.

19. The rasp as recited in claim 18 and further comprising a measuring scale on said shaft for indicating the depth of said head portion within said intervertebral space.

20. The rasp as recited in claim 18 and wherein said upper face has a more acute curvature than said lower face in order to more closely complement the natural intervertebral disc space in which the upper, downwardly directed bone plate has a greater concavity than the concavity of the lower, upwardly directed bone plate.

21. The rasp as recited in claim 6 wherein said rasp is an intervertebrally operated vertebral bone plate shaping rasp having a rasp surface on at least a portion of both said upper and said lower faces and wherein said outwardly disposed surface is substantially smooth.

22. The rasp as recited in claim 21 and further comprising a measuring scale on said shaft for indicating the depth of said head portion within said intervertebral space.

23. The rasp as recited in claim 21 and wherein said upper face has a more acute curvature than said lower face in order to more closely complement the natural intervertebral disc space in which the upper, downwardly directed bone plate has a greater concavity than the concavity of the lower, upwardly directed bone plate.

24. The rasp as recited in claim 21 and wherein said outwardly disposed surface has a maximum dimension extending between said upper and said lower face at an anterior side of said head portion and a minimum dimension extending between said upper and said lower face at a posterior side of said head portion, to account for the natural lordosis in said intervertebral space between two adjacent vertebral bone plates.

25. The rasp as recited in claim 24 wherein said shaft extends from said head portion substantially collinear with a line extending from said from said posterior side of said head portion to thereby form an anterior procedure rasp.

26. The rasp as recited in claim 24 wherein said shaft extends from said head portion at an angle with respect to a line extending from said from said posterior side of said head portion to thereby form an anterolateral procedure rasp.

27. The rasp as recited in claim 6 and wherein said outwardly disposed surface has a maximum dimension extending between said upper and said lower face at an anterior side of said head portion and a minimum dimension extending between said upper and said lower face at a posterior side of said head portion, to account for a natural lordosis in said intervertebral space between two adjacent vertebral bone plates.

28. The rasp as recited in claim 27 wherein said shaft extends from said head portion substantially collinear with a longitudinal axis extending from said posterior side of said head portion to thereby form an anterior procedure rasp.

29. The rasp as recited in claim 27 wherein said shaft extends from said head portion at an angle with respect to a longitudinal axis extending from said posterior side of said head portion to thereby form an anterolateral procedure rasp.

30. The rasp as recited in claim 29 wherein said angle from which said shaft extends from said head portion with respect to said longitudinal axis extending from said from said posterior side of said head portion is from about 20° to about 70°.

31. A rasp for use in spine surgery comprising:
a head portion for fitting within an intervertebral space between two adjacent vertebral bone plates and having an upper face and a lower face and an outwardly disposed surface extending between said upper and said lower face, and wherein at least a portion of one of said upper face, said lower face and said outwardly disposed surface includes a rasp surface;
a shaft extending from said outwardly disposed surface to permit said head portion to be angularly displaced at least slightly within said intervertebral space; and
a locking slot on said shaft and further comprising a handle portion and wherein said handle portion has a slot and a locking ring at least partially extending into said slot to engage said locking slot when said second end of tip portion is inserted into a blind bore at a front end of said handle portion.

32. The rasp as recited in claim 31 and wherein said handle portion is at least partially hollow is oval at least to the extent of a transverse rectangular oval shape.

33. A rasp for use in spine surgery comprising:
a circular head portion for fitting within an intervertebral space between two adjacent vertebral bone plates and having an upper face and a lower face and an outwardly disposed surface extending between said upper and said lower face, and wherein at least a portion of one of said upper face, said lower face and said outwardly disposed surface includes a rasp surface; and
a shaft extending from said outwardly disposed surface to permit said head portion to be angularly displaced at least slightly within said intervertebral space, and
wherein said rasp is a roughing combination rasp having a rasp surface on at least a portion of said outwardly disposed surface and upon on at least a portion of at least one of said upper and said lower faces, so that said circular head portion may be rotated about a center to remove intervertebral material.

34. The rasp as recited in claim 33 and further comprising a measuring scale on said shaft for indicating a depth of said head portion within said intervertebral space.

35. The rasp as recited in claim 33 and wherein said upper and said lower faces are convex for complementing a naturally biconcave intervertebral disc space.

36. The rasp as recited in claim 35 and wherein said upper face has a more acute curvature than said lower face in order to more closely complement a natural intervertebral disc space in which an upper, downwardly directed bone plate has a greater concavity than a concavity of a lower, upwardly directed bone plate.

37. The rasp as recited in claim 33 and wherein said outwardly disposed surface has a maximum dimension extending between said upper and said lower face at an anterior side of said head portion and a minimum dimension extending between said upper and said lower face at a posterior side of said head portion, to account for a natural lordosis in said intervertebral space between two adjacent vertebral bone plates.

38. The rasp as recited in claim 37 wherein said shaft extends from said head portion substantially collinear with a longitudinal axis extending from said posterior side of said head portion to thereby form an anterior procedure rasp.

39. The rasp as recited in claim 37 wherein said shaft extends from said head portion at an angle with respect to a longitudinal axis line extending from said posterior side of said head portion to thereby form an anterolateral procedure rasp.

* * * * *